US008226992B1

(12) United States Patent
Okerlin, III

(10) Patent No.: US 8,226,992 B1
(45) Date of Patent: Jul. 24, 2012

(54) COMPOSITION AND METHOD OF PREVENTING AND TREATING REDOX DISEASES

(76) Inventor: John R. Okerlin, III, Tampa, FL (US)

( * ) Notice: Subject to any disclaimer, the term of this patent is extended or adjusted under 35 U.S.C. 154(b) by 198 days.

(21) Appl. No.: 12/775,903

(22) Filed: May 7, 2010

Related U.S. Application Data

(60) Provisional application No. 61/215,602, filed on May 7, 2009.

(51) Int. Cl.
*A01N 65/00* (2009.01)

(52) U.S. Cl. ........................................................ 424/725

(58) Field of Classification Search ........................ None
See application file for complete search history.

(56) References Cited

PUBLICATIONS

Lee et al. 2007. "Hepatoprotective and antioxidant effects of the coffee diterpenes kahweol and cafestol on carbon tetrachloride-induced liver damage in mice." Food and Chemical Toxicology. vol. 45. pp. 2118-2125.
Huber et al. 2006. "Oxidative stress and acute toxicity cause by the alkylating carcinogen azoxyrnethane in rat liver are inhibited by the coffee diterpenes kahweol and cafestol." Proc. Amer. Assoc. Cancer Res. vol. 47.
Huber et al. 2005. "Modification of N-acetyltransferases and glutathione S-transferases by coffee components: Possible relevance for cancer risk." Methods in Enzymology. vol. 401. pp. 307-341.
Kim et al. 2006. "Inhibitory effect of the coffee diterpene kahweol on carrageenan-induced inflammation in rats." BioFactors. vol. 26. pp. 17-28.
Choi et al. 2006. "Protective effect of the coffee diterpenes kahweol and cafestol on tert-butyl hydroperoxide-induced oxidative hepatotoxicity." Bull. Korean Chem. Soc. vol. 27 No. 9. pp. 1386-1392.
Kim et al 2006 "The coffee diterpene kahweol inhibits tumor necrosis factor-alpha-induced expression of cell adhesion molecules in human endothelial cells." Toxicology and Applied Pharmacology. vol. 217. pp. 332-341.
Majer et al. 2005. "Coffee diterpenes prevent the genotoxic effects of 2-amino-l-methyl-phenylimidazo[4,5-b]pyridine (PhIP) and N-nitrosodimethylamine in a human derived liver cell line (HepG2)." Food and Chemical Toxicology. vol. 43. pp. 433-441.
Steinkellner et al. 2005. "Coffee consumption induces GSTP in plasma and protects lymphocytes against (+/−)-anti-benzo[alpha]pyrene-7,8-dihydrodiol-9,10-epoxide induced DNA damage: Results of controlled human intervention trials." Mutation Research. vol. 591. pp. 264-275.
Pool-Zobel et al. 2005. "Modulation of xenobiotic metabolising enzymes by anticarcinogens-focus on glutathione S-transferases and their role as targets of dietary chemoprevention in colorectal carcinogenesis." Mutation Research. vol. 591. pp. 74-92.
Boekschoten et al. 2005. "Coffee oil consumption increases plasma levels of 7alpha-hydroxy-4-cholesten-3-one in humans." J. Nutr. vol. 135. pp. 785-789.
Boekschoten et al. 2004. "Coffee bean extracts rich and poor in kahweol both give rise to elevation of liver enzymes in healthy volunteers." Nutrition Journal. vol. 3. No. 7. pp. 1-8.
Kim et al. 2004. "The coffee diterpene kahweol suppress the inducible nitric oxide synthase expression in macrophages." Cancer Letters. vol. 213. pp. 147-154.
Kim et al. 2004. "Suppressive effects of the kahweol and cafestol on cyclooxygenase-2 expression in macrophages." FEBS Letters. vol. 569. pp. 321-326.
Huber et al. 2004. "Potential chemoprotective effects of the coffee components kahweol and cafestol palmitates via the modification of hepatic N-acetyltransferase and glutathione S-transferase activities." Environmental and Molecular Mutagenesis. vol. 44. pp. 265-276.
Iannaccone. 2005. "Environmental medicine: where are we and where do we go from here? (you can't navigate from lost)." Environmental Health Perspectives. Accessed Aug. 2, 2010 from http://www.thefreelibrary.com/Environmental+medicine%3a+where+are+we+and+where+do+we+go+from+here%3f...-a0144351008.
Turesky et al. 2003. "The effects of coffee on enzymes involved in metabolism of the dietary carcinogen 2-amino-1-methyl-6-phenylimidazo [4,5-b]pyridine in rats." Chemico-Biological Interactions. vol 145. pp. 251-265.
Esposito et al. 2003. "Moderate coffee consumption increases plasma glutathione but not homocysteine in healthy subjects." Aliment Pharmacol Ther vol. 17 pp. 595-601.
Somoza et al. 2003. "Activity-guided identification of a chemoprotective compound in coffee beverage using in vitro and in vivo techniques." J. Agric. Food Chem. vol. 51. pp. 6861-6869.
Scharf et al. 2003. "Enhancement of glutathione an gamma-glutamylcysteine synthetase, the rate limiting enzyme of glutathione synthesis, by chemoprotective plant-derived food and beverage components in the human hepatoma cell line HepG2." Nutrition and Cancer. vol. 45. No. 1. pp. 74-83.
Cavin et al. 2003. "Coffee diterpenes prevent benzo[a]pyrene genotoxicity in rat and human culture systems." Biochemical and Biophysical Research Communications. vol. 306. pp. 488-495.

(Continued)

*Primary Examiner* — Michael Meller
(74) *Attorney, Agent, or Firm* — Robert Varkonyi; Smith & Hopen, P.A.

(57) ABSTRACT

Methods and compositions useful for preventing the disruption of thiol (sulfur) signaling which affects degenerative/age related disease and other disease states related to thiol redox signaling, such as S-glutathiolation. The compositions are capable of increasing the DNA transcription of Gamma-Glutamyl-cysteine synthase which is the rate limiting enzyme for the production of the thiol regulating enzyme Glutathione. The acid-stable compositions disclosed herein contain esterfied and free form cafestol and kahweol, and may be formed using ground roasted or unroasted coffee beans. The beans in combination with water are exposed to cavatonic energy sonic or mechanical. C&K typically increase cholesterol and damage the liver. The compositions disclosed are absorbed before or after the distal portion of the small intestines, eliminating liver toxicity and increases in cholesterol. Additional materials may be added to the compositions, such as additional hydrophobic compounds hydrophilic compounds, and may be added to the film or embedded in the compositions by the cavitation process. The process is also adapted for use in all standard methods of brewing coffee, causing the coffee to possess the disclosed compositions.

12 Claims, 5 Drawing Sheets

PUBLICATIONS

Huber et al. 2003. "Coffee and its chemoprotective components kahweol and cafestol increase the activity of O6-methylguanine-DNA methyltransferase in rat liver—comparison with phase II xenobiotic metabolism." Mutation Research. vol. 522. pp. 57-68.
Boekschoten et al. 2003. "Reproducibility of the serum lipid response to coffee oil in healthy volunteers." Nutrition Journal. vol. 2. No. 8. pp. 1-8.
Hammar et al. 2003. "Association of boiled and filtered coffee with incidence of first nonfatal myocardial infarction: The SHEEP and the VHEEP study." Journal of Internal Medicine. vol. 253. pp. 653-659.
Huber et al. 2002. "Enhancement of the chemoprotective enzymes glucuronosyl transferase and glutathione transferase in specific organs of the rat by the coffee components kahweol and cafestol." Arch. Toxicol. vol. 76. pp. 209-217.
Cavin et al. 2002. "Cafestol and Kahweol, two coffee specific diterpenes with anticarcinogenic activity." Food and Chemical Toxicology. vol. 40. pp. 1155-1163.
McMahon et al. 2001. "The cap 'n' collar basic leucine zipper transcription factor Nrf2 (NF-E2 p45-related Factor 2) controls both constitutive and inducible expression of intestinal detoxification and glutathione biosynthetic enzymes." Cancer Research. vol. 61. pp. 3299-3307.
Grubben et al. 2000. "The effect of unfiltered coffee on potential biomarkers for colonic cancer risk in healthy volunteers: A randomized trial." Aliment Pharmacol. Ther. vol. 14 pp. 1181-1190.
Van Zeeland et al. 1999. "8-Hydroxydeoxyguanosine in DNA from leukocytes of healthy adults: relationship with cigarette smoking, environmental tobacco smoke, alcohol and coffee consumption." Mutat. Res. vol. 439. No. 2. pp. 249-257.
Cavin et al. 1998. "The coffee specific diterpenes cafestol and kahweol protect against aflatoxin B1-induced genotoxicity through a dual mechanism." Carcinogenesis. vol. 19. No. 8. pp. 1369-1375.
De Roos et al. 1998. "Absorption and urinary excretion of the coffee diterpenes cafestol and kahweol in healthy ileostomy volunteers." Journal of Internal Medicine. vol. 244, pp. 451-460.
Schilter et al. 1996. "Placental glutathione S-transferase (GST-P) induction as a potential mechanism for the anti-carcinogenic effect of the coffee-specific components cafestol and kahweol." Carcinogenesis. vol. 17. No. 11. pp. 2377-2384.
De Roos et al. 2000. "Consumption of French-press coffee raises cholesteryl ester transfer protein activity levels before LDL cholesterol in normolipidaemic subjects." Journal of Internal Medicine. vol. 248. pp. 211-216.
Urgert et al. 1997. "Diterpenes from coffee beans decrease serum levels of lipoprotein(a) in humans: results from four randomised controlled trials." European Journal of Clinical Nutrition. vol. 51. pp. 431-436.
Urgert et al. 1996. "Comparison of effect of cafetiere and filtered coffee on serum concentrations of liver aminotransferases and lipids: six month randomised controlled trial." BMJ. vol. 313. pp. 1362-1366.
Urgert et al. 1997. "The cholesterol-raising factor from coffee beans." Annu. Rev. Nutr. vol. 17. pp. 305-324.
Bonaa et al. 1998. "Coffee and cholesterol: Is it all in the brewing? The Tromso study." BMJ. vol. 297, pp. 1103-1104.
Ranheim et al. 1995. "Effect of a coffee lipid (cafestol) on regulation of lipid metabolism in CaCo-2 cells." Journal of Lipid Research. vol. 36. pp. 2079-2089.
Van Rooij et al. 1995. "A placebo-controlled parallel study of the effect of two types of coffee oil on serum lipids and tansaminases: identification chemical substances in the cholesterol raising effect of coffee." The American Journal of Clinical Nutrition. vol. 61. No. 6. pp. 1277-1283.
Mensink et al 1995. "Diterpene composition of oils from Arabica and Robusta coffee beans and their effects on serum lipids in man." Journal of Internal Medicine. vol. 237 pp. 543-550.
Turgut et al. 2009. "Letter to the Editor. Gamma-glutamyltransferase as a useful predictor for cardiovascular risk: Clinical arid epidemiological perspectives." Atherosclerosis. vol. 202. pp. 348-349.
Strasak et al. 2008. "Longitudinal change in serum gamma-glutamyltransferase and cardiovascular disease mortality: A prospective population-based study in 76, 113 Austrian adults." Alterioscler. Thromb. Vasc. Biol. vol. 28. No. 10. pp. 1857-1865.
Lee et al, 2008. "Association of serum gamma-glutamyltranferase with C-reactive protein levels and white blood cell count in Korean adults." Clin. Chem. Lab. Med. vol. 46. No. 10. pp. 1410-1415.
Zoppini et al. 2008 "Original Article: Metabolism Relationship between soluble CD40 ligand and gamma-glutamyltransferase concentrations in non-drinking, young Type 1 diabetic individuals." Diabetic Medicine. vol. 25. pp. 1283-1288.
Strasak et al. 2008. "Prospective study of the association of gamma-glutamyltransferase with cancer incidence in women." Int. J. Cancer. vol. 123. pp. 1902-1906.
Devers et al. 2008. "Should liver function tests be included in definitions of metabolic syndrome? Evidence from the association between liver function tests, components of metabolic syndrome and prevalent cardiovascular disease." Diabetic Medicine. vol. 25. No. 5. pp. 523-529.
Strasak et al. 2008. "Association of gamma-glutamyltransferase and risk of cancer incidence in men: a prospective study." Cancer Res. vol. 68. No. 10. pp. 3970-3977.
Wannamethee et al. 2008. "The value of gamma-glutamytransferase in cardiovascular risk prediction in men without diagnosed cardiovascular disease or diabetes." Atherosclerosis. vol. 201. pp. 188-175.
Franzini et al. 2009. "Gamma-Glutamyltransferase activity in human atherosclerotic plaques—Biochemical similarities with the circulating enzyme." Atherosclerosis. vol. 202. pp. 119-127.
Giral. et al. 2008. "Elevated gamma-glutamyltransferase activity and perturbed thiol profile are associated with features of metabolic syndrome." Arterioscler. Thromb. Vasc. Biol. vol. 28. pp. 587-593.
Lee et al. 2008. "Is serum gamma-glutamyltransferase a biomarker of xenobiotics, which are conjugated by glutathione." Aterioscler. Thromb. Vasc. Biol. vol. 28. pp. e26-e28.
Yavuz et al. 2008, "Serum elevated gamma glutamyltransferase levels may be a marker for oxidative stress in Alzheimer's disease." International Psychogeriatrics, vol. 20, No. 4., pp. 815-823.
Lee et al. 2007. "Gamma glutamyl transferase and metabolic syndrome, cardiovascular disease, and mortality risk. The Framingham heart study." Arterioseler. Thromb. Vasc. Biol., vol. 27., pp. 127-133.
Lippi et al. 2007. "Short communication. Relationship between gamma-glutamyltransferase, lipids and lipoprotein(a) in the general population." Clinica Chimica Acta, vol. 384, pp. 163-166.
Hiramatsu et al. 2007. "Overexpression of {gamma}-glutamyltransferase in transgenic mice accelerates bone resorption and causes osteoporosis." Endocrinology, vol. 148, pp. 2708-2715.
Pompella et al. 2007. "Gamma-Glutamyltransferase, redox regulation and cancer drug resistance." Current Opinion in Pharmacology, vol. 7, pp. 360-366.
Kotani et al 2008. "Letter to the Editor. Changes in serum gamma-glutamyltransferase and blood pressure levels in subjects with normal blood pressure and prehypertension." Clinica Chemica Acta, vol. 389, pp. 189-190.
Shankar et al. 2007. "Association between serum gamma-glutamyltransferase level and prehypertension among US adults." Circulation Journal, vol. 71, pp. 1567-1572.
Grundy. 2007. "Gamma-glutamyl transferase. Another biomarker for metabolic syndrome and cardiovascular risk." Arterioscler. Thromb. Vasc. Biol., vol. 27, pp. 4-7.
Kazemi-Shirazi et al. 2007. "Gamma glutamyltransferase and long-term survival: is it list the liver?" Clinical Chemistry, vol. 53, No. 5, pp. 940-946.
Asaba et al. 2006. "Urinary gamma-glutamyltransferase (GGT) as a potential marker of bone resorption." Bone, vol. 39, pp. 1276-1282.
Emdin et al. 2006. "Gamma-glutamyltransferase as a cardiovascular risk factor." European Heart Journal, vol. 27, pp, 2145-2146.
Ryu et al. 2007. "Gamma-glutamyltransferase as a predictor of chronic kidney disease in nonhypertensive and nondiabetic Korean men." Clinical Chemistry, vol. 53, No. 1, pp. 71-77.
Paolicchi et al. 2006. "Beta Lipoprotein- and LDL-associated serum gamma-glutamyltransferase in patients with coronary atherosclerosis." Atherosclerosis, vol. 186, pp. 80-85.

Ruttmann et al. 2005. "Gamma-glutamyltransferase as a risk factor for cardiovascular disease mortality. An epidemiological investigation in a cohort of 163 944 Austrian adults." Circulation, vol. 112, 2130-2137.
Emdin et al. 2005. "Gamma-glutamyltransferase, atherosclerosis, and cardiovascular disease. Triggering oxidative stress within the plaque." Circulation, vol. 112, pp. 2078-2080.
Paolicchi et al. 2004. "Human atherosclerotic plaques contain gamma-glutamyl transpeptidase enzyme activity." Circulation, vol. 109, p. 1440.
Pompella et al. 2004. "Opinion paper. The significance of serum gamma-glutamyltransferase in cardiovascular diseases." Clin. Chem. Lab. Med., vol. 42, No. 10, pp. 1085-1091.
Djavaheri-Mergny et al. 2002. "Gamma-glutamyl transpeptidase activity mediates NF-kB activation through lipid peroxidation in human leukemia U937 cells." Molecular and Cellular Biochemistry, vol. 232, pp. 103-111.
Whitfield et al. 2002. "Genetic Covariation between serum gamma-glutamyitransferase activity and cardiovascular risk factors." Clinical Chemistry, vol. 48, No. 9, pp. 1426-1431.
Emdin et al. 2001. "Prognostic value of serum gamma-glutamyl transferase activity after myocardial infarction." European Heart Journal, vol. 22, pp. 1802-1807.
Mason et al. 2010. "Review paper. Gamma-glutamyl transferase: a novel cardiovascular risk biomarker." Preventive cardiology, vol. 13, No. 1, pp. 36-41.
Stojakovic et al. 2010. "Serum gamma-glutamyl transferase and mortality in persons undergoing coronary angiography—The Ludwigshafen Risk and Cardiovascular Health Study." Atherosclerosis, vol. 208, pp. 564-571.
Breitling et al. 2010. "Gamma-glutamyltransferase and prognosis in patients with stable coronary heart disease followed over 8 years." Atherosclerosis, vol. 210, pp. 649-655.
Shimizu et al. 2010. "Gamma-glutamyltranspeptidase and incident stroke among Japanese men and women. The Circulatory Risk in Communities Study (CIRCS)." Stroke, vol. 41, pp. 385-388.
Franzini et al. 2010. "Cardiovascular risk factors and gamma-glutamyltransferase fractions in healthy individuals." Clinical Chemistry and Laboratory Medicine, vol. 48, pp. 713-717.
Sen et al. 2009. "Relationship between elevated serum gamma-glutamytransferase activity and slow coronary flow." Arch. Turk. Soc. Cardiol., vol. 37, No. 3, pp. 168-173.
Poelzl et al. 2009. "Prevalence of elevated gamma-glutamyltransferase (GGT) and prognostic significance of GGT in chronic heart failure." Circulation: Heart Failure, http://circheartfailure.ahajournals.org/cgi/content/short/CIRCHEARTFAILURE.108.826735v1, accessed on Aug. 2, 2010.
Korantzopoulos et al. 2009. "Association between serum gamma-glutamyltransferase and acute ischemic nonembolic stroke in elderly subjects." Archives of Medical Research, vol. 40, pp. 582-589.
Turgut et al. 2009. "Association of gamma-glutamyitransferase with cardiovascular risk: a prognostic outlook." Archives of Medical Research, vol. 40, pp. 318-320.
Emdin et al. 2009. "Additive prognostic value of gamma-glutamyltransferase in coronary artery disease." International Journal of Cardiology, vol. 136, pp. 80-85.
Lee et al. 2009. "Serum gamma-glutamyltransferase: new insights about an old enzyme." J. Epidemiol. Community Health, vol. 63, pp. 884-886.
Lee et al. 2009. "Multiple biomarkers and their relative contributions to identifying metabolic syndrome." Clinica Chimica Acta, vol. 408, pp. 50-55.
Fraser et al. 2009. "Alanine aminotransferase, gamma-glutamyltransferase, and incident diabetes." Diabetes Care, vol. 32, No. 4, pp. 741-750.
Ruhl et al. 2009. "Clinical advances in liver, pancreas, and biliary tract. Elevated serum alanine aminotransferase and gamma-glutamyltransferase and mortality in the United States population." Gastroenterology, vol. 136, pp. 477-485.
Nemesanszky et al. 1985. "Gamma-glutamyltransferase and its isoenzymes: progress and problems." Clin. Chem., vol. 31, No. 6, pp. 797-803.
Davis. 2008. "What your doctor didn't tell you about lipoprotein(a)." http://www.healthcentral.com/heart-disease/c/1435/44295/lipoprotein, accessed on Aug. 2, 2010.
Gordon. 2010, "Little-known fat can be a heartbreaker, Elevated lipoprotein (a) levels boost cardiovascular disease risk for some." ABC News Internet Ventures, http://abcnews.go.com/Health/Healthday/story?id=6006953&page=1, accessed on Aug. 4, 2010.
Bergmark et al. 2008. "A novel function of lipoprotein [a] as a preferential carrier of oxidized phospholipids in human plasma" Journal of Lipid Research, vol. 49, 2230-2239.
Jones 2008. "Lipoprotein(a) and coronary artery disease:" HCPlive, http://www.hcplive.com/cardiology/publications/cardiology-review-online/2008/july2008/July-2008-Jones-commentary, accessed on Aug. 2, 2010.
Bennet et al. 2008. "Lipoprotein(a) levels and risk of future coronary heart disease. Large-scale prospective data." Arch. Intern. Med., vol. 168, No. 6, pp. 598-608.
Staples et al. 2008. "Exceptional Case. Progressive kidney disease in three sisters with elevated lipoprotein(a)." Nephrol Dial Transplant, vol. 23, pp. 1756-1759.
Petersen et al. 2007. "Lp(a) lipoprotein and plasminogen activity in patients with different etiology of ischemic stroke." Cerebrovasc, Dis., vol. 23, pp. 188-193.
Jones et al 2007. "Plasma lipoprotein(a) indicates risk for 4 distinct forms of vascular disease." Clinical Chemistry, vol. 53, No. 4, pp. 679-685.
Uhlig. 2005. "Cross-sectional characterization of lipoprotein(a) in chronic kidney disease." Tufts University, Sackler School of Graduate biomedical Sciences, thesis submitted May 2005.
Lippi et al. 2003. "Lipoprotein(a): an emerging cardiovascular risk factor." Critical Reviews in Clinical Laboratory Sciences, vol. 40, No. 1, pp. 1-42.
Ariyo et al. 2003. "Lp(a) lipoprotein, vascular disease, and mortality in the elderly." N. Engl. J. Med., vol. 349, No. 22. pp. 2108-2115.
Pan et al. 2002. "Extended-release niacin treatment of the atherogenic lipid profile and lipoprotein(a) in diabetes." Metabolism, vol. 51, No. 9, pp. 1120-1127.
Pan et al. 2002. "Niacin treatment of the atherogenic lipid profile and Lp(a) in diabetes." Diabetes, Obesity and Metabolism, vol. 4, pp. 255-261.
Edelberg et al. 1992. "Why is lipoprotein(a) relevant to thrombosis?" Am. J. Clin. Nutr., vol. 56, pp. 791S-792S.
Sedda et al. 2008. "Plasma glutathione levels are independently associated with gamma-glutamyltransferase activity in subjects with cardiovascular risk factors." Free Radical Research, vol. 42, No. 2, pp. 135-141.
Ballatori et al. 2009. "Gluthathione dysregulation and the etiology and progression of human diseases." Biol. Chem., vol. 390, No. 3, pp. 101-214.
Hill et al 2008. "Role of gluthathiolation in preservation, restoration and regulation of protein function." International Union of Biochemistry and Molecular Biology, Inc., vol. 59, No. 1, pp. 21-26.
Zhang et al. "Gamma-gluthamyl transpeptidase in glutathione biosynthesis." Method in Enzymology, vol. 41. pp. 468-479.
Zee et al., "Redox Regulation of Sirtuin-1 by S-Glutathiolation," Antioxid. Redox Signal, 2010, epub. ahead of print.
Hwang et al., "The coffee diterpene kahweol induces heme oxygenase-1 via the PI3K and p38/Nrf2 pathway to protect human dopaminergic neurons from 6-hydroxydopamine-derived oxidative stress," FEBS Letters, 2008, vol. 582, pp. 2655-2662.
Borgstrom. 1967. "Partition of lipids between emulsified oil and micellar phases of glyceride-bile salt dispersions." Journal of Lipid Research. vol. 8. pp. 598-808.
Marciani et al 2007. "Enhancement of intragastric acid stability of a fat emulsion meal delays gastric emptying and increases cholecystokinin release and gallbladder contraction." Am. J. Physiol. Gastrointest. Liver Physiol. vol. 292. pp. G1607-G1613.
"Soxhlet Extractor"Accessed Aug. 2, 2010. Wikipedia. http://en.wikipedia.org/wiki/soxhlet_extractor.
Jones. 2008. "Radical-free biology of oxidative stress." Am. J. Physiol. Cell. Physiol. vol. 295. pp. C849-C868.
Cimino et al. 2008. "Glutathione metabolism: Favorable versus unfavorable effects." Oxidants in Biology. Chapter 10. pp. 203-229.

Van Der Vliet et al. 2008. "Cellular and environmental electrophiles: Balancing redox signaling, inflammation, and cell death pathways." Oxidants in Biology. Chapter 3. pp. 37-66.
Townsend. 2007. "S-Glutathionylation indicator of cell stress and regulator of the unfolded protein response." Molecular Interventions. vol. 7. Issue 6. pp. 313-324.
Livingstone et al. 2007. "Targeting therapeutics against glutathione depletion in diabetes and its complications." Br. J. Diabetes Vasc. Dis. vol. 7. pp. 258-265.
Mira, et al. 2007. "Anti-oxidant and anti-atherogenic properties of liposomal glutathione: Studies in vitro, and in the atherosclerotic apolipoprotein E-deficient mice." Atherosclerosis. vol. 195. pp. e61-e68.
Gutierrez et al. 2006. "Free radicals, mitochondria, and oxidized lipids: The emerging role in signal transduction in vascular cells." Circ. Res. vol. 99. pp. 924-932.
Rossi et al. 2006. "Oxidized forms of glutathione in peripheral blood as biomarkers for oxidative stress." Clinical Chemistry. vol. 52. No. 7. pp. 1406-1414.
Ashfaq et al. 2006. "The relationship between plasma levels of oxidized and reduced thiols and early Atherosclerosis in healthy adults." J. Am. Coll. Cardiol. vol. 47, No. 5. pp. 1005-1011.
Sampathkumar et al. 2005. "Increased glutathionylated hemoglobin (HbSSG) in type 2 diabetes subjects with microangiopathy." Clinical Biochemistry. vol. 38. pp. 892-899.
Niture. et al. 2005. "S-Thiolation mimicry: Quantitative and kinetic analysis of redox status of protein cysteines by glutathione-affinity chromatography." Archives of Biochemistry and Biophysics. vol. 444. pp. 174-184.
Zilmer et al. 2005. "The glutathione system as an attractive therapeutic target." Drug Design Reviews—Online. vol. 2. No. 2. pp. 121-127.
Santanam et al. 1995. "Cellular cysteine generation does not contribute to the initiation of LDL oxidation." J. Lipid Res. vol. 36. pp. 2203-2211.
Bageman et al. 2008. "Coffee consumption and CYP1A2*1F genotype modify age at breast cancer diagnosis and estrogen receptor status." Cancer Epidemiol. Biomarkers Prev. vol. 17. No. 4 pp. 895-901.
American College of Physicians. 2008. "Coffee drinkers have slightly lower death rates, study finds." ScienceDaily. Retrieved Aug. 2, 2010 from http://www.sciencedaily.com/releases/2008/06/080616170839.htm.
Hu et al. 2008. "Joint effects of coffee consumption and serum gamma-glutamyltransferase on the risk of liver cancer." Hepatology. vol. 48. pp. 129-136.
Wiley-Blackwell. 2008. "Higher coffee consumption associated with lower liver cancer risk." ScienceDaily. Retrieved Aug. 2, 2010 from http://www.sciencedaily.com/releases/2008/06/080626150926.htm.
La Vecchia. 2008. "Cancer and liver cancer prevention: Is it a fact or just a potential?" vol. 48. No. 1. pp. 7-9.
Happonen et al. 2008. "Coffee consumption and mortality in a 14-year follow-up of an elderly northern Finnish population." British Journal of Nutrition. vol. 99. pp. 1354-1361.
Kotani et al. 2008. "The relationship between usual coffee consumption and serum C-reactive protein level in a Japanese female population." Clin. Chem. Lab Med. vol. 46. No. 10. pp, 1434-1437.
Cadden et al. 2007 "Review article: Possible beneficial effects of coffee on liver disease and function." Aliment Pharmacol. Ther. vol. 26. pp. 1-7.
Groch. 2007. "Analysis validates reduced risk of liver cancer by coffee drinking." MedPage Today, Retrieved Aug. 2, 2010 from http://www.medpagetoday.com/Gastromterology/GeneralHepatology/6324.
Reinberg. 2010 "Coffee may lower liver cancer risk." ABC News. Retrieved Aug. 2, 2010 from http://abcnews.go.com/Health/Healthday/story?id=4508156&page=1.
Colorectal Cancer Association of Canada. 2007. "Coffee drinking no longer so controversial."Retrieved Aug. 2, 2010 from http://www.colorectal-cancer.ca/en/news-and-resources/coffee-controversial/?var_recherche=coffee%20drinking.
John Wiley & Sons, Inc. 2007. "Drinking four cups of coffee a day may help to prevent gout." ScienceDaily. Retrieved Aug. 2, 2010 from http://www.sciencedaily.com/releases/2007/05/07052507.htm.
Larsson et al. 2007. "Coffee consumption and risk of liver cancer: A meta-analysis." Gastroenterology. vol. 132. pp. 1740-1745.
Kraft Foods Global Nutrition. 2007. "Health benefits of coffee: A review of existing and emerging science." www.kraftnutrition.com. pp. 1-6.
Bravi et al. 2007. "Coffee drinking and hepatocellular carcinoma risk: A meta-analysis." Hepatology. vol. 36. pp. 430-435.
Silletta et al. 2007. "Coffee consumption and risk of cardiovascular events after acute myocardial infarction: Results from the GISSI (Gruppo Italiano per lo Studio della Sopravvivenza nell'Infarto miocardico)-Prevenzione trial," Circulation. vol. 116. pp. 2944-2951.
McAvoy et al. 2006. "Coffee is good for the liver." J. R. Coll. Physicians Edinb. vol. 36. pp. 32-34.
Rosner et al. 2006. "Coffee consumption and risk of myocardial infarction among older Swedish women." Am. J. Epidemiol. vol. 165. No. 3. pp. 288-293.
Ranheim et al. 2005. "Coffee consumption and human health—beneficial or detrimental?—Mechanisms for effects of coffee consumption on different risk factors for cardiovascular disease and type 2 diabetes mellitus." Mol. Nutr. Food. Res. vol. 49. pp. 274-284.
Van Dam et al. 2005. "Coffee consumption and risk of type 2 diabetes—A systematic review." JAMA. vol. 294. No. 1. pp. 97-104.
La Vecchia. 2005. "Coffee, liver enzymes, cirrhosis and liver cancer." Journal of Hepatology. vol. 42. pp. 444-446.
Tuomilehto et al. 2004. "Coffee consumption and risk of type 2 diabetes mellitus among middle-aged Finnish men and women." JAMA. vol. 291. No. 10. pp. 1213-1219.
Gallus et al. 2002. "Does coffee protect against liver cirrhosis?" Ann. Epidemiol. vol. 12. pp. 202-205.
Grubben et al. 2000. "Unfiltered coffee increases plasma homocysteine concentrations in healthy volunteers: A randomized trial(1-3)." Am. J. Clin. Nutr. vol. 71. pp. 480-484.
Giovannucci. 1998. "Meta-analysis of coffee consumption and risk of colorectal cancer." Am J. Epidemiol. vol. 147. No. 11. pp. 1043-1052.
Baron et al. 1994. "Coffee, tea, tobacco, and cancer of the large bowel." Cancer Epidemiology, Biomarkers & Prevention. vol. 3. pp. 565-570.
Pintos et al. 1994. "Maté coffee, and tea consumption and risk of cancers of the upper aerodigestive tract in southern Brazil." Epidemiology. vol. 5. No. 6. pp. 583-590.
Casiglia et al. 1993. "Unexpected effects of coffee consumption on liver enzymes." Eur. J. Epidemiol. vol. 9. No. 3. pp. 293-297.
Salminen et al. 2008. "Terpenoids: Natural inhibitors of NF-KappaB signaling with anti-inflammatory and anticancer potential." Cell. Mol. Life Sci. vol. 65. pp. 2979-2999.
Higgins et al. 2008. "Induction of cancer chemopreventive enzymes by coffee is mediated by transcription factor Nrf2. Evidence that the coffee-specific diterpenes cafestol and kahweol confer protection against acrolein." Toxicology and Applied Pharmacology. vol. 226. pp. 328-337.
Huber et al. 2008. "Effects of coffee and its chemoprotective components kahweol and cafestol on cytochrome P450 and suffotransferase in rat liver." Food and Chemical Toxicology. vol. 46. pp. 1230-1238.
Ricketts et al. 2007. "The cholesterol raising factor from coffee beans, cafestol, as an agonist ligand for the famesoid and pregnane x receptors." Molecular Endocrinology. vol. 21. No. 7. pp. 1603-1616.
Bichler et al. 2007. "Coffee consumption protects human lymphocytes against oxidative and 3-amino-1-methyl-5H-pyrido[4,3-b]indole acetate (Trp-P-2) induced DNA-damage: Results of an experimental study with human volunteers." Food and Chemical Toxicology. vol. 45. pp. 1428-1436.
Cavin et al. 2007. "Reduction in antioxidant defenses mav contribute to Ochratoxin A toxicity and carcinogenicity." Toxicological Sciences. vol. 96. No. 1. pp. 30-39.

COMPOSITION AND METHOD OF PREVENTING AND TREATING REDOX DISEASES

CROSS REFERENCE TO RELATED APPLICATION

This application claims priority to pending U.S. Provisional Patent Application No. 61/215,602, entitled "Method(s) and Composition(s) of New Compounds that Regulate Thiol Redox which in Turn Prevent or Reduce all Degenerative and Age Related Disease Directly or Indirectly Associated with Thiol Redox Regulation", filed on May 7, 2009, the contents of which are herein incorporated by reference.

FIELD OF INVENTION

This invention relates to prevention and/or correction of degenerative diseases and/or disease states caused by the loss of thiol redox signaling. Specifically, the invention uses natural small therapeutic molecule complexes.

BACKGROUND OF THE INVENTION

Cell signaling is part of a vital communications network allowing cells to perceive and correctly respond to their microenvironment it is the basis of development, tissue repair, and cell functioning. Signals are generated, received, and transcribed by intracellular, transcellular and extracellular enzymes and proteins. It has been recently shown that the majority of proteins and enzymes in a mammal contain functional thiol (sulfur) groups, mainly in the form of the amino acid cysteine. These proteins and enzymes communicate with each other through redox reactions. In a redox reaction there are always two simultaneous reactions; an oxidation and a reduction. These redox sensitive thiol reactions are involved in almost every aspect of life, such as; energy regulation, cytoskeletal structure, transport, proliferation, differentiation and apoptosis. Without this communication life could not continue.

New dogma states that oxidative stress and chronic inflammation is the results of the body's inability to prevent the disruption of thiol circuits (Jones 2008). When non-radical compounds like hydrogen peroxide interfere with this communication flow, that is, they steal electrons, unbalancing cellular homeostasis. Once unbalanced, cells begin to produce pro-oxidant compounds including more hydrogen peroxide, resulting in additional oxidative stress. One of the major transcriptional pathways that produced pro-oxidants is the Nuclear Factor Kappa-Beta (NF-κB) pathway. This entire cascade of events produces a negative feedback loop within a cell or specific cells that can be local or systemic in an organ or the entire body. This negative feedback results in low level chronic inflammation, which then progresses over time into some form of degenerative or so called age related disease, such as atherosclerosis, cardiovascular diseases (CVDs), cancer, Alzheimer's disease, Type 1 and 2 Diabetes, liver cirrhosis or liver disease, Rheumatoid arthritis, osteoporosis, Irritable Bowl Syndrome, cataract disease, cystic fibrosis, asthma, hypertension, dementia, Parkinson's disease, gout, multiple sclerosis (MS), Lupis, and sepsis.

In this chronic inflammation state, the stated thiol(s) are either losing electrons to non-radical compounds or they are in a dormant non-reactive state because they have been protected by s-glutathiolation. Glutathiolation has emerged as an important post-translational modification that prevents irreversible oxidation of protein thiols, and recent evidence suggests that controlled glutathiolation reactions can also be used to modify protein structure and function. Reduced glutathione remains bound to reactive cysteine side chains of several intracellular proteins even under basal conditions and the abundance of glutathiolated proteins increases upon oxidant challenge (Hill & Bhatnagar, Role of glutathiolation in preservation, restoration and regulation of protein function. IUBMB Life. 2007 January; 59(1):21-6). These glutathiolated thiols can also be in a disulfide state, where bridging with other enzyme and proteins produces a disulfide bond. Also while in this state both proteins and enzymes can be incorrectly folded (via internal disulfide bonds). Regardless, in these states they are non-functional or they are functioning in a negative was towards life.

Recently, Resveratrol has been shown to be inhibited by S-nitrosoglutathione (GSNO) which resulted in S-gutathiolation of sirtuin-1 (Zee R S, Antioxidant Redox Signaling: 2010 online prior to publication). Since the small molecule complexes of this invention regulate thiol redox and thiol redox drives S-glutathiolation a conclusion can be drawn that this invention will help promote the therapeutic activities of Resveratrol by preventing and/or reducing S-glutathiolation. Following this logic the complexes in this invention can be used to enhance drugs and supplements that are subject to S-glutathiolation either directly or within the cellular pathway they are targeted for.

In the regulation of thiol redox it should be noted that this also extends to cover proteins and enzymes that are inactivated through S-glutathiolation/S-glutathionylation. A list of some of these proteins include actin, spectrin, tubulin, vimentin, glyceraldehyde-3phosphate dehydrogenase (GAPDH), phosphoglycerate kinase, triose phosephate insomerase, pyruvate kinase, aldolase, alpha-ketoglutarate dehydrogenase, mitochondiral isocritrate, dehydrogenase, complex 1, NADHP, ATPase, NADH ubiquinone reductase, carbonic anhydrase III, catechol-O-methyltransferase, pyruvate dehydrogenase, MEKK1 (JNK), protein tyrosine phosphatase 1B, PTEN, pyrophosphatase 2A, Nuclear Factor Kappa Beta (NF-kB) subunits 65 and 50, PKC, PKG, (cAMP) dependent PKA, creatinine kinase, c-able, p53, caspase 3, GTPase p21 ras, S1000A1 and S100B, SERCA, ryanodine receptor I and II, CTFR, PDI, HSP 65,70, 20S proteosome, ubiquitin conjugating enzyme, thioredoxin 1, glutathione S-transferase An example some of the diseases associate with S-glutathiolation are listed in Table 1.

TABLE 1

A correlation of diseases related to different protein dysfunction in humans.

| Protein | Disease |
|---|---|
| Actin | Cardiovascular/Ischmia |
| Tau | Alzheimer's disease |
| Hemoglobin | Type 2 diabetes |
| CTFR | Cystic Fibrosis |
| γ-S-crystallin | Cataract disease |
| Spectrin | Sickle cell anemia |

It has been discovered that Glutathione (GSH) is responsible for maintaining thiol redox in mammals. GSH is found throughout the body and with age or exposure to xenobiotic (foreign) compounds (organisms, such as bacteria, viruses, or carcinogens, or other compounds the body does not make) decreases. Decreases in intracellular GSH have been shown to be directly related to disease states and or progression to disease states such as; Cardiovascular Diseases, Autoimmune Diseases, Pulmonary Diseases, Cystic Fibrosis, Lupus, Crohn's Disease, Type I Diabetes, Type II Diabetes/Diabetes Mellitus, Psoriasis, Contact Dermatitis, Multiple Sclerosis, Liver Diseases, and Viral Infections. (Sedda 2008) and (Ballatori 2009) Therefore, increasing intracellular levels of GSH through therapeutic means is desirable. GSH is produced by the intracellular enzyme Gamma-Glutamyl-cysteine synthase (GCS). GCS, however, can only be produced through DNA transcription, via the Nuclear Factor-Erythroid 2 p45-related Factor (Nrf2) pathway. Importantly, GCS is the rate limiting enzyme in GSH production. However, basic activation of Nrf2 doesn't guarantee the transcription of GCS.

While GCS is the rate limiting enzyme for the production of GSH the enzyme Gamma Glutamyltransferase, also know as Gamma Glutamyl Transpeptidase (GGT), is also involved in GSH production. GGT is a membrane bound enzyme that plays a key role in GSH production by transporting the required building block amino acids into the cell. It also transports GSH conjugated xenbiotic compounds out the cell. Importantly, the increase expression of GGT has been shown to be directly associated with a decrease in GSH while a decrease in GGT is associated with GSH increases or a steady state. (Zhang 2005, Ballatori 2009) GGT is therefore, directly involved in the regulation of thiol redox via the glutathione cycle. Thiol redox regulation is required to ensure that cell signaling pathways are maintained. Dysfunction of cell signaling leads to the pathogenesis of many human diseases (Yardimci, Clincal and Applied Thrombosis, 1995:1:2:103-113).

GGT has been used as a biomarker for predicting alcohol abuse and bile tract obstruction for over 30 years. However, modern research into oxidative stress and cell signaling has discovered that this enzyme has been misclassified, overlook and underutilized. In fact, GGT has become a primary biomarker for oxidative stress and for all cause of mortality. Elevations in GGT are seen in almost all chronic and life-style related diseases, such as oxidative stress, metabolic syndrome, Type II diabetes, fatty liver disease, cardiovascular diseases, Alzheimer's disease, liver cirrhosis, chronic kidney disease and cancer (Mason, Preventive Cardiology 2010: 13:1:36-41; Stojakovic, Atherosclerosis 2010: 208:2:564-571; Breitling, Atherosclerosis 2010: Jan. 11 Online 2010; Shimizu, Stroke AHA 2010: 41:385-388; Franzini, Medicine 2010: Online February 2010; Sen, Turkish Society of Cardiology 2009: 37:168-173; Poelzl, Circulation: Heart Failure 2009: 2:294-302; Korantzopoulos, Archives of Medical Research 2009: 40:7:582-589; Turgut, Archives of Medical Research 2009: 40:4:381-320; Emdin, International Journal of Cardiology, 2009: 136:1:80-85; Lee, International Journal of Clincal Chemistry 2009; 408:1-2; Abigail, Diabetes Care 2009: 32:4741-750.). Recently, the National Institutes of Health (NIH) has shown that elevated levels of GGT increase all cause mortality death rates in the United States (US) (Constance, Gasteroenterology 2009: 136:477-485). In fact, one of the most negative trends associated with elevated levels of GGT is its association with death. More importantly, GGT has been discovered to play a key role in the pathogenesis and progression of Atherosclerosis and Osteoporosis.

Recently, it has been discovered that GGT acts as a cytokine (a signaling molecule) when it comes to the initiation of osteoclast production. Mice genetically modified to over express GGT have major bone deformities, are dwarfs and died early as a result of accelerated osteoporosis Importantly, when collagen induced arthritic mice were treated with an Anti-Glutamyl Transpeptidase Antibody, osteoporosis was attenuated and in some cases reversed. In humans, extreme elevated levels of GGT are found in individuals with primary biliary cirrhosis (PBC). These individuals have an increased risk of Osteoporosis. Alcoholics can also have elevated levels of GGT and the prevalence of osteoporosis is higher in alcoholics. Interestingly, bone loss is halted or is reversed in alcoholics that abstain for up to 6 months.

Oxidized LDL (ox-LDL) is known to initiate the pathogenesis of Atherosclerosis. In blood serum, GGT is found unbound or it can be found bound to lipoproteins. Importantly, it has been shown that GGT oxidizes LDL from its enzymatic activity: Cisteinly-Glycine+Iron forms hydrogen peroxide which oxidizes LDL and activates NF-kB, a pro-oxidant intracellular pathway. By oxidizing LDL GGT becomes a direct participant in the pathogenesis of atherosclerosis. Additionally, increased oxidized LDL levels also increase Lipoprotein (a) (Lp(a)) levels. Lp(a) is a known confounding biomarker for Cardiovascular Diseases.

Finally, GGT has been discovered in arterial plaque. Once embedded in plaque it not only continues to oxidize LDL, but it is capable of signaling osteoclast development which leads to calcification. Increases in ox-LDL increases Lp(a) levels and individuals with elevated levels of Lp(a) have an increased risk of coronary artery calcification. Interestingly, elevated levels of GGT in individuals with recent coronary stent implantation indicate stent failure. Also, serum GGT is predictive of all-cause and cardiovascular death in individuals with coronary artery disease (CAD) independently of other cardiovascular risk factors.

Combining the above three GGT discoveries sets up a chain of events that are simultaneously detrimental to both bone and vascular health. As noted above, GGT oxidizes LDL, which increases Lp(a) and initiates osteoporosis. GGT also increases osteoclast development, accelerating bone loss. As atherosclerosis progresses, plaques are formed, which are attacked by the increased osteoclast population, resulting in the calcification of the plaque and increase in mortality. The interaction is cyclical, further propogating the disease.

Taking the above discussion into account, a method to reduce GGT would be a major step in assisting with slowing the initiation and progression of Atherosclerosis, Osteoporosis and possible other vascular and inflammatory diseases such as Type II Diabetes. At this time, there are no FDA approved drugs or supplements that can significantly reduce GGT. In fact, as xenobiotic compounds the basic metabolism of drugs and supplements actually produces oxidative stress and thus decreases the intracellular levels of GSH which increases GGT expression. Since GGT levels are directly associated with GSH levels and GSH levels are tied to the rate limiting transcriptional enzyme GCS the focus on reducing GGT expression should be centered on increasing the expression of GCS.

Most xenobiotic compounds will temporarily increase GSH, via a cascade of events that activates/simulates/signals GCS to produce GSH. These xenobiotic compounds are seen as invaders to the cell and therefore GSH production is increased. This increase however, can't be sustained unless the rate-limiting enzyme GCS is increased (transcribed/expressed through the Nrf2 pathway) prior to GSH production. If GCS is not increased prior to GSH the cell is placed in a lag phase where the production of GSH is always lagging behind the concentration of whatever compound(s) are attacking the cell. This lag phase produces an environment where non-radicals continue to disrupt thiol signaling. In this lag phase GSH level drop and upstream expression of GGT increases. Most importantly, in this state cross talk between multiple transcriptional pathway is lost or misdirected leaving some pathways to constantly transcribe compounds. For example in this state the NF-κB pathway may continually produce pro-oxidants that in turn continually add to the non-radical load of the cell. On the other hand, the Nrf2 pathway can be silent, thereby preventing production of oxidation-protective enzymes. Ultimately the homeostasis of the cell's thiol signaling is lost.

To realistically increase GSH, the rate-limiting enzyme GCS must be increased (transcribed) prior to any increases in GSH. Since xenobiotic compounds increase GSH it is difficult to find therapeutic compounds that increase GCS prior to GSH production. Hundreds of compounds have been tested around this requirement. Of all the compounds tested, in the available literature, only two compounds have been identified that increase GSC prior to GSH. Those two compounds are the small therapeutic molecules (STMs) Cafestol and Kahweol (C&K) (Scharf 2003).

C&K are diterpenes which may be isolated from the oil of the coffee bean, where they are found bonded to a single fatty acid group (they are esterfied). These fatty acids can vary by type, such as C14, C16, C18, C18:1, C18:2, C18:3, C20, C22 and C24. In their pure forms they are unstable and susceptible to breakdown from heat. Interestingly, just as GGT has been discovered to be associated with the increased risk in Cardiovascular Disease, Fatty Liver Disease, Type II Diabetes, Metabolic Syndrome, Liver Cirrhosis, Alzheimer's/Dementia and Cancer, the consumption of coffee at 6 or more cups per day has been shown to reduce the risk of these same diseases. Studies indicate that drinking 6 or more cups per day increase overall life spans or decrease overall morality rates, and high coffee consumption has also been shown to reduce both GGT and Lp(a) by up to 15%. C & K were identified in coffee in the late 1980s. During this period, methods of coffee preparation were also tested to identify the amounts of C & K contained in each extraction method, seen in Table 2.

TABLE 2

The concentration of extracted from coffee beans using various extraction methods. The tests were based on 180 ml water and 10 grains of ground coffee beans.

| Method of Extraction | Amount of C & K (mg) |
|---|---|
| Filtered | 0.2 |
| Percolated | 0.2 |
| Instant | 0.4 |
| Espresso | 3.3 |
| Mocha | 2.5 |
| Boiled | 6.9 |
| French | 7.9 |
| Turkish/Greek | 7.8 |

As seen in Table 2 filtered coffee was shown to have very little C & K in it; 0.2 mg per cup, mainly because the filter removes any of the oil extracted from the coffee bean. This may be the primary reason it take up to 6 cups of coffee per day to see the health benefits of drinking coffee. It should be noted that hot water or steam alone is not an effective method for the removal/extraction of the hydrophobic compounds found in the coffee bean. Though not seen in Table 2, when pure coffee oil is extracted from 10 grams of ground coffee beans using an organic solvent, such as hexane, the analysis of the coffee oil indicates that it contains approximately 1800 mg of C & K, or about 9000 times the amount found in one cup of filtered coffee.

Cafestol and Kahweol have been identified by several laboratory research studies to upregulate Nrft2, which conjugates toxic compounds and removes them from the cell; and to downregulate NF-κB, which prevents the expression of chronic inflammation compounds such as COX-2 or iNOS. The disclosed compositions will logically possess the same characteristics, such as limiting diseases that are connected to each of these pathways, such as, cancer caused by exposure to toxic environmental compounds.

C&K activate or upregulate Nrf2 which signals the DNA to produces Phase II enzymes, such as GCS, responsible for generating GSH; Glutathione S-Tranferase (GST), which generates GST-P. GST-As, GST-Ms; Quinon Oxidoreductases such as NQO1 or NADPH; UDP-Glucoronosyl-Transferase (UGT); Heme Oxygenase-1 (HO1); sulfotransferases [SULTs]; acetyltransferases [NAT1&2]; and methyl transferase. These Phase II enzymes are known to be cancer preventative proteins involved in the detoxification (conjugation) of carcinogenic xenobiotic compounds, some of which are persistent organic pollutants (POPs) that are encountered through diet or other exposure methods such as breathing and/or adsorption.

Laboratory studies have shown that C&K are protective against carcinogens or suspected carcinogens such as carbon tetrachloride; azoxymethane; N-Nitrosodimethylamine (NDMA), an industrial byproduct from rocket fuel found as a low-level contaminant in food and in water; acrolein, which is a byproduct from degradation of tobacco, gasoline, fried food, and cooking oil; HeteroCyclic Aromatic Amines (HAA or HCA), which are a degradation byproduct of foods prepared with heat; pyridine (PhIP), found in cooked meat and fish; benzo[α]pyrene, found in coal tar, tobacco smoke, charbroiled foods and burnt toast; aflatoxin B1, a mold toxin found in spoiled grains; 6-OHDA, a causative Parkinson's disease agent in laboratory mice. It is noted that any compound that can reduce the damage from CCL4 may have a significant role in maintaining health when used as medicine or consumed as a part of the normal diet.

C&K also inhibit or down-regulate the transcription factor NF-κB, which is responsible for signaling the DNA to produce pro-oxidant enzymes such as inducible Nitric Oxide Synthase (iNOS), Prostaglandin E Synthase-2 (PGE-2) and Cyclooxygenase-2 (COX-2). These destructive enzymes are part of a response that keep cells proliferating and protects them from apoptosis. However, acute inflammation process can become chronic with constant activation of NF-κB. In fact elevated levels of iNOS, PGE-2, COX-2 and NF-κB are associated with Chronic Inflammatory Diseases, such as; Alzheimer's disease, Parkinson's disease, atherosclerosis, inflammatory bowel disease, rheumatoid arthritis, multiple sclerosis, sepsis, osteoporosis autoimmune disease, asthma, hypersensitivities (such as allergies), pelvic inflammatory disease, Rosacea, transplant rejection, and other chronic inflammatory diseases. Additionally, Chronic Inflammation has recently been shown to be directly linked to cancer.

C&K are also intracellular and extracellular SuperOxide Scavengers, that is they are involved in reducing non-radicals such as hydrogen peroxide and tert-Butyl hyperoxide.

Ironically, though C&K can increase GCS prior to GSH demand, act as intracellular antioxidants, upregulate Nrf2 Phase II enzyme production and downregulate, NF-κB pro-oxidant production, these compounds have been shown to also increase cholesterol and damage the liver. Testing of C&K in individuals who consumed unfiltered coffee, coffee oil or coffee grinds revealed that C&K increased cholesterol and liver damage. Increases in cholesterol have been associated with increased in cardiovascular diseases (CVDs), while liver damage leads to possible cirrhosis, liver failure, and death. Recently, in the mouse model Cafestol was shown to be an agonist ligand for Farnesoid X Receptors (FXR). (Ricketts 2007) These receptors are located in the distal portion or ileum portion of the small intestine in most mammals including humans. Activation of FXR activates the recirculation of bile acids which can increase cholesterol and damage the liver.

In a 1996 study, coffee and coffee oil containing high concentrations of C&K raised the liver inflammation enzyme alanine aminotransferase (ALT) by 35 units per liter (U/L) on average in test subjects. In fact several subjects were removed from the study because their elevations were above the ALT cutoff level 53.5 U/L. Low density lipoprotein cholesterol concentrations in subjects rose by 9-14% relative to filtered coffee and triglyceride concentrations initially rose by 26%, but returned close to baseline within 6 months (Urgert, Br Med J, 1996). Coffee oil (Arabica), in a 2003 study on liver enzymes, showed that C&K dramatically raised ALT and aspartate aminotraseferase (AST) levels. In this study extreme ALT elevation were observed at 3.6, 5.8 & 12.4 times the cutoff of 45U/L, while AST elevations were observed at 2.0 and 4.7 times the cutoff of 50 U/L. (Boekschoten 2004). These facts prompted the medical community and certain government agencies throughout the world to warn people about the dangers of drinking unfiltered coffee and consuming coffee oil. Ultimately, the use of C&K or coffee oil as supplements to regulate thiol redox via the amplification of GCS along with the amplification of the Nrf2 pathway has been ignored because of the stated negative biological issues in humans. As discussed earlier C&K amplify the Nrf2 pathway thus they increase the transcription of many different Phase II enzymes such as the Glutathione Transferases Family which are involved in detoxification by conjugating xenobiotic/toxic electrophiles to GSH for their removal from the cell. Because these Phase II enzymes required GSH amplifying their expressions does not provide health benefits to the cell if GSH is not increased through the amplification of the expression of GCS. Without this type of increase the Phase II enzymes will use up the intracellular GSH pool. Therefore, targeting GCS for amplification is also required for Phase II enzyme optimization.

However, there are currently no acceptable compounds for modulating GCS prior to GSH demand and preventing and correcting diseases associated with GCS reduction, GSH reduction and GGT increases. Accordingly, the present invention addresses these important needs.

SUMMARY OF THE INVENTION

Disclosed are methods and compositions useful for preventing the disruption of thiol (sulfur) signaling in mammals which ultimately reduces or prevents all degenerative and age related disease and any other physiological states that are directly and/or indirectly related to thiol redox regulation or are produced by the reduction or loss in the production/transcription of the intracellular enzyme Gamma-Glutamyl-cysteine synthase (GCS), along with its end product the enzyme Glutathione (GSH) and the increase expression GGT.

The compositions “colloidal suspensions” or “precipitated suspensions” disclosed herein contain C&K in their esterfied form and/or free form. A process floss diagram of how the composition can be generated is seen in FIG. 7.0. The compositions may be formed using ground roasted or unroasted coffee beans. The beans can be fresh or previously hydrated/washed (used). Regardless, the beans are washed in water, followed by exposing the hydrated bean grounds to cavatonic energy. The ratio of grounds to water ranging from 1 g:2 ml to 1 g:40 ml. While the wash may be conducted at any temperature, is has been discovered to be especially useful at between about 71° C. to about 100° C. In particular, the amount of time required to wash the bean grounds is positively correlated to the temperature, though the wash is generally conducted for between about 1 minute to 72 hours. The concentration levels of hydrophilic coffee compounds in the wash can range from highly concentrated to very weak or almost no hydrophilic compounds. A Soxhlet extraction may optionally be used to adjust concentration levels remaining in the grounds. This process removes almost all of the hydrophilic compounds leaving only hydrophobic and soluble fibers that are still bound to the insoluble hydrated bean fiber.

The temperature of the bean grounds/liquid are at about 0° C. to about 100° C. for the sonication or cavation process. With the ratio of grounds to water ranging from 1 g:2 ml to 1 g:40 ml. In certain embodiments, maximum extraction of all compounds is obtained at higher temperatures. It is noted that any cavitation technique may be used, such as an ultrasonic horn, ultrasonic whistle or a homogenating valve. In certain variations, the cavatonic sonic energy added is from between 15 Khz to 100 Mhz, and may be at 40 Mhz at 200 watts. The cavitated solution is allowed to settle, and is filtered. The coffee beans can be ground from coarse-ground to powdered ground. The hydrated bean grounds are exposed to the cavatonic energy for from about 1 second to about 72 hours.

Additional materials may be added to the composition, such as additional hydrophobic compounds hydrophilic compounds, proteins polysaccharides, melanoidins, cysteine, glycine, glutamate, glutamine, N-acetylcysteine, methionine, synthetic GSH, natural polysulfides, diallyltrisulfide, diallyltetrasulfide, or combinations thereof. The added composition or combination thereof may be added to the hydrated bean grounds prior to the bean grounds exposition to cavatonic energy to allow for the cavitation process to emulsify the added materials with the disclosed compositions. These compounds can also be added after initial sonication/cavitation and reprocessed with the same sonication/cavitation. This allows these compounds to be attached as a film or as part of the existing film or embedded into the structures produced during intial cavatation or secondary cavatation. Likewise, the composition may be added to a base food product, such as flavored coffee, instant coffee, tea, yogurt, cheese, dairy, orange juice, sports drinks, sports gels, or pills.

In specific embodiments, the composition is incorporated into a pill or capsule. To incorporate the composition into a solid body such as a capsule the composition is exposed to 75% alcohol. At least 50% of the composition’s volume is required to produce precipitate. The resulting precipitate is then centrifuged and the alcohol removed through evaporation or freeze drying. The resulting slurry can then be extruded into to capsules or into other food products or sports gels.

In is noted that a scaled down version of this procedure may be used for non-commercial preparation, albeit with lower yields. The inclusion of a cavitation system can be incorporated into all of today’s standard methods of brewing coffee, causing the coffee to possess at least one or more of the complexes described below. Standard methods included filtered coffee makers, espresso machines and new single cup machines. Sonication to produce cavitation shall occur in all machines where coffee grind and water interface. Accordingly, a machine is disclosed for brewing coffee using the cavitation method. The machine comprises a first receptacle adapted to hold liquid. A heating element adapted to spontaneously heat the liquid from about 25° C. to about 100° C., is in fluid communication with the first receptacle, thereby allowing the machine to change the temperature of the liquid if necessary. A second receptacle is used to hold coffee grind and will also house a cavitation device. When coffee bean grounds are added and water and/or steam from the first receptacle is moved to the second receptacle, the cavitation device will provide the caviation energy discussed above, thereby generating the disclosed compositions. A third receptacle is used to collect the brewed liquid, in fluid communication with the second receptacle. The cavitation device may be any device known to generate cavitation, such as wherein the cavatonic energy generating device is a sonicator, ultrasonic whistle or homogenating valve. Additionally, the cavatonic energy generating device may be programmed to subject the coffee bean grounds to cavatonic energy for a specified period of time, or energy bursts for a specified period of time, as is known in the art. Alternatively, water, heating element, grind and cavitiation device can be located in one receptacle where the receptacle can be a batch process and it can include a coffee ground slurry recycle loop that can house the cavitation device. While filtering can be accomplished by centrifugal or passive filtering.

The compositions described herein can also be used to correct or prevent a degenerative disease or age-related disease in a patient. A therapeutic of the disclosed composition is generated, as described above, and a therapeutically effective amount administered to the patient. This has been found particularly useful for diseases such as cardiovascular disease, fatty liver disease, Type II diabetes, metabolic syndrome, liver cirrhosis, Alzheimer's disease, Parkinson's disease, dementia, and cancer.

BRIEF DESCRIPTION OF THE DRAWINGS

For a fuller understanding of the invention, reference should be made to the following detailed description, taken in connection with the accompanying drawings, in which.

DETAILED DESCRIPTION OF THE PREFERRED EMBODIMENT

Figure 1:
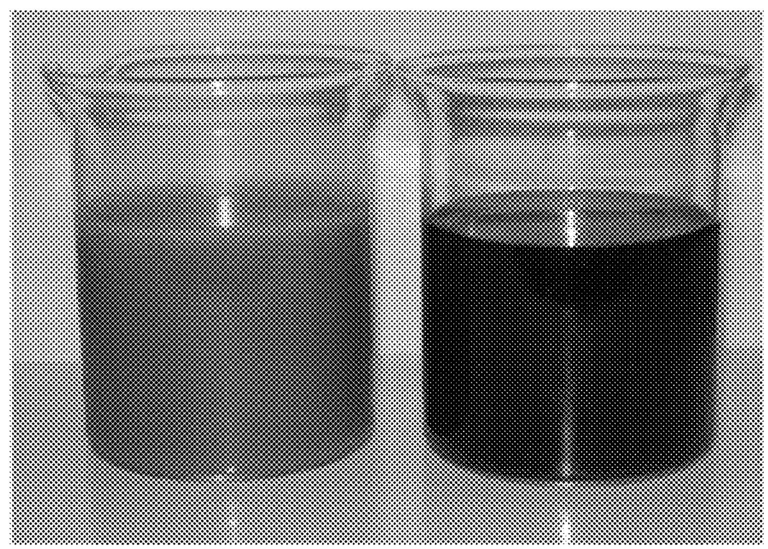
FIG. 1 is an image comparing untreated versus treated (colloidal suspension-added) coffee drink

The present invention notes the novel observation that when ground coffee beans and water (hot or cold) are exposed to cavitation, such as ultrasonic energy or homogenating mechanical energy, hydrophobic and hydrophilic compounds extracted from the beans produce unique compositions that contain new structures as part of an acid/base stable colloidal suspension. These new structures/compounds contain esterfied C&K and/or free form C&K and other therapeutic compounds. When orally consumed these new structures can be used to regulate thiol redox without increasing cholesterol or damaging the liver. In fact in-vivo testing indicates that these unique composition(s) actually significantly reduce the biomarkers associated with liver inflammation and damage.

As used herein, "microscopic particles" means; Micro-Coffee Micelles (MCMs), which are hydrophilic micelle spheres containing C&K esterfied or free from that range in size from 0.01 μm to 25 μm in diameter; Micro-Hydrophobic proplets (MHDs), hydrophobic droplets that range in size from 1.0 μm to 100 μm that contain C&K esterfied or free from; Micro-Embedded Compounds (MECs), which are soluble fiber polysaccharide and/or melanoidin compounds embedded with C&K esterfied or free and other hydrophobic and hydrophilic compounds which are less than 0.1 μm in diameter. MCMs and MHDs also optionally can have amino acids, proteins, non-digestible polysaccharides, melanoidins and other therapeutic and non-therapeutic compounds coated or embedded within the film of the MCMs and MHDs or as part of a new film coating the original film. Caffeine can also be bound or embedded into the macro-molecular structures of MEC or soluble fiber film of MCMs and MHDs. This embedment allows caffeine to move to the large intestine without being absorbed in the small intestine. Caffeine studies with these compositions indicate that the half-life of caffeine is greatly enhanced because additional caffeine is released into the blood stream anywhere from 3 to 7 hours after consumption or once the compounds enter the colon and are slowly digested by the colon bacteria.

The Micro-Coffee Micelles (MCMs) contain esterfied C&K and or free form C&K and other hydrophobic compounds as part of their structure. The MCMs spheres possess a water-soluble surface area instead of a hydrophobic surface area. Because coffee also contains both proteins and polysaccharides/melanoidins these compounds can become part of the micelle or they can coat the micelle. This gives the composition and the MCMs additional stability and unique digestible qualities.

The Micro-Embedded Compounds (MECs), which contain esterfied C&K and or free form C&K and other hydrophobic/hydrophilic compounds embedded in the soluble fiber polysaccharide and/or melanoidin compounds found in coffee, are digested only in the colon. MECs are not digestible in the small intestines.

Micro-Hydrophobic proplets (MHDs), which contain esterfied C&K and or free form C&K and other hydrophobic compounds, possess spherical hydrophobic surface areas that don't coalesce. Both proteins and/or polysaccharides and/or melanoidins coat some of the structures. This coating assists in stability and also produces unique digestible qualities.

As used herein, "cavitation" means a method or process wherein vapor bubbles are formed in a liquid by the introduction of sonic energy or mechanical energy. These bubbles rapidly collapse producing a shock wave. Examples of sonic energy include sound and ultrasound. Sound waves typically used in cavitation procedures range 20 kHz to 100 kHz. Ultrasound was used at 20 kHz-12.5 mHz, and in specific examples at 40 kHz. Examples of mechanical energy are rotating/vibrating homogenization devices. These technologies are commonly employed in both the food and pharmaceutical industries.

The term "patient" or "individual" includes mammals and non-mammals. Non-limiting examples include humans, non-human primates, species of the family bovidae, species of the family suidae, domestic animals including rabbits, dogs, and cats, laboratory animals, such as rats, mice, guinea pigs, and non-mammals, including birds and fish.

As used herein, "correcting" means any manner in which the symptoms or pathology of a condition, disorder or disease are ameliorated or otherwise beneficially altered.

As used herein "prevent" means reducing the occurrence of or ameliorating the causative elements of the pathology of a condition, disorder or disease is beneficially altered prior to the occurrence of symptoms.

In general, the compounds of the present invention are administered in a therapeutically effective amount by any accepted mode of administration. Suitable dosage ranges depend upon factors known to one skilled in the art. Non-limiting examples of factors include the severity of the disease to be treated, or prevented the age of the patient, the relative health of the subject, the potency of the compound utilized, and the route and form of administration. One skilled in the art will also be capable of ascertaining the therapeutically effective amount of compound needed for a given disease, without undue experimentation and in reliance of his or her experience.

The use of cavitation generates microscopic particles containing at least esterfied C&K and or free form Cafestol and Kahweol. These compositions are unique because the energy applied to the mixture extracts and produces three different types of unique structures MCMs, MHDs and MECs, that contain esterfied C&K and or free form C&K in a colloidal suspension These unique compositions can be used in combinations with each other or they can be used as an independent single composition. Additionally, adding other non-coffee compounds or adding additional coffee compound to the coffee beans, grounds or liquid solution shall be covered or claimed as part of each of the compositions. Some of these added compounds could become part of the micelles structure or could be encapsulated within the micelles: MCMs. The compounds can also become embedded in the MECs as well or they can become part of the MHDs. Additional films and embedment on each unique structure is enhanced by additional cavitation steps. Those skilled in the art of emulsion and colloidal chemistry would be capable of modifying each composition.

A colloidal suspension/coffee drink was prepared, as described in Example 1. The colloidal suspension's end product visually appears to have cream already added to it due to the cavitation technique, as seen in FIG. 1. However, this is not cream but the mass quantity of Microscopic Particles in the colloidal suspension. The compositions contain very little free-phase oil, if any, and if present, this oil is removed by filtering. When filtered, the micro-sized components that contain esterfied and free form C&K and other hydrophobic compounds pass through the filter, based on their size. The porosity of a coffee filter is around 100-150 μm while the micro sized components of the composition(s) range from 0.1-40 μm. The uniform size distribution and quantities of the compositions are determined by processing time and power input.

More importantly, the micro-sized components pass through the filter because they are a colloidal suspension. As a colloidal suspension the micro-sized components do not present a hydrophobic surface area, and therefore do not stick to other non-water-soluble substances like the coffee bean itself or filter paper. Instead the micro-sized components present a hydrophilic or water-soluble surface area, which allows them to pass through a filter.

Figure 2:
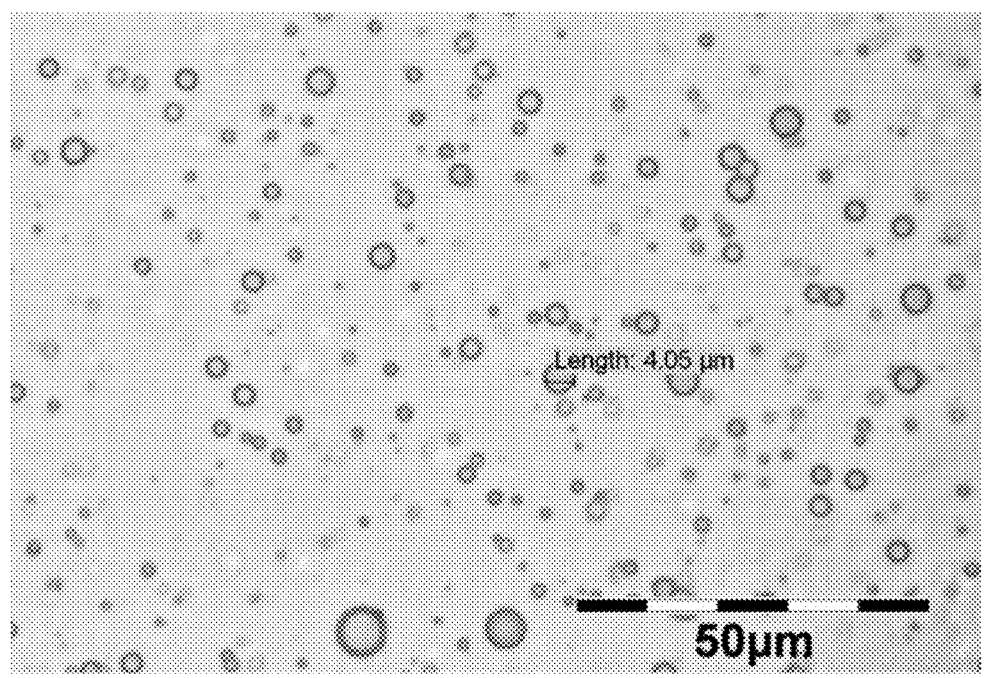
FIG. 2 is a microscopic image of the colloid composition 5 minutes after the suspension was filtered using a 20 μm filter.
Figure 3:
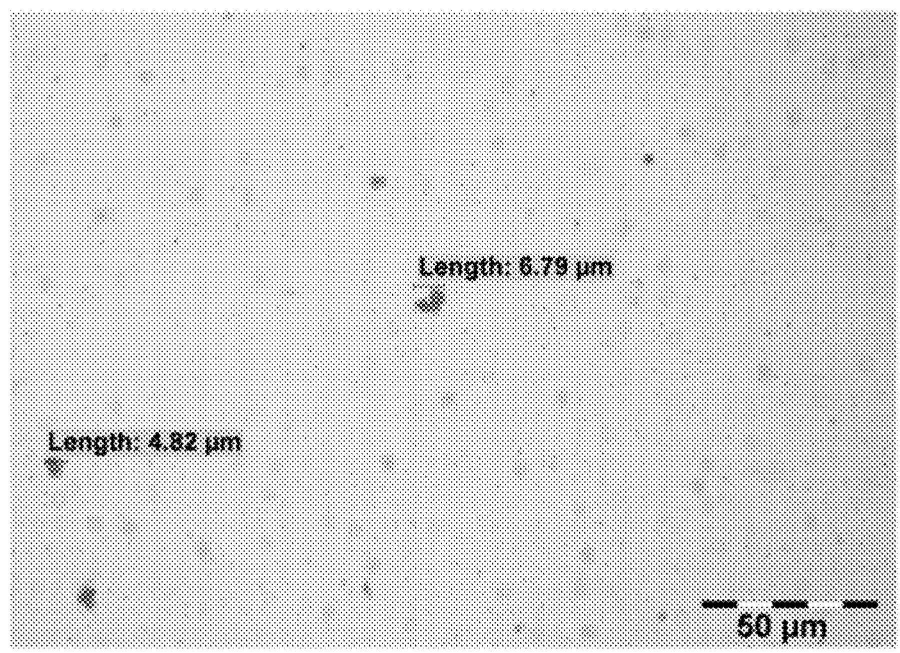
FIG. 3 is a microscopic image of unfiltered espresso coffee, without the colloidal suspension.
Figure 4:
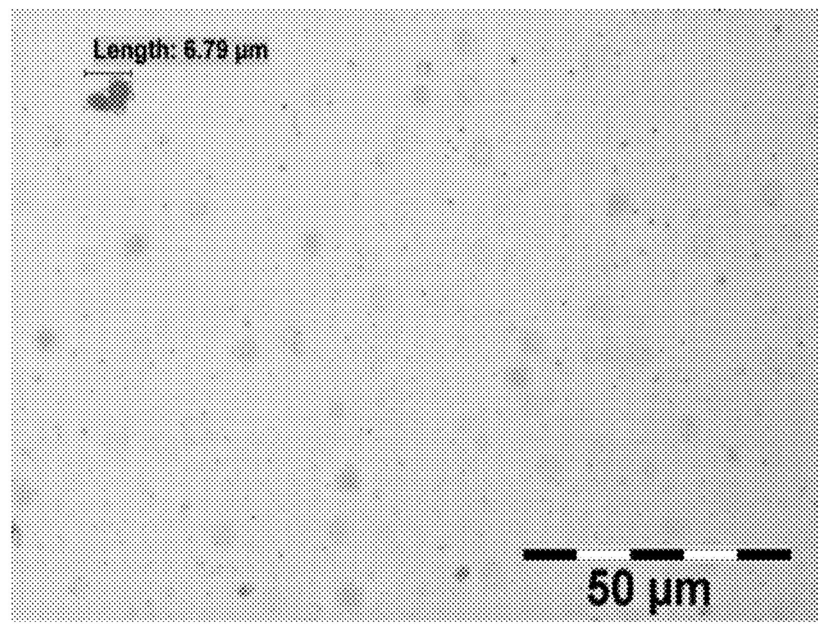
FIG. 4 is an enlarged view of a microscopic image of unfiltered espresso coffee, without the colloidal suspension.

FIG. 2 shows the microscopy of one of the said compositions filtered at 20 μm. Under microscopy, Brownain Movement was visible, further indicating the stability of the colloidal suspension. As a comparison unfiltered espresso coffee was also examined, seen in FIG. 3. There are very few structures observed, there was no Brownain Movement observed, and the compounds present, aside from trash, were coalescing into clumps, as seen in FIG. 4. This indicates that the few structures present in the espresso sample were droplets of oil that were aggregating with each other. Further, while the energy of steam can create some mixed MHDs, as seen in FIG. 3, the amount produced is negligible. Hot water and steam are not effective at removing the hydrophobic compounds in and on the coffee bean, as oil does not dissolve in water. Moreover the mixed MHDs formed are aggregating to from larger structures, as seen in FIG. 4. This indicates that these few structures are unstable. Additionally, the small amounts of hydrophobic compounds removed with the use of hot water or steam are still hydrophobic and they will attach/stick to other surfaces such as the paper filter. Additionally, filtering an espresso removes the majority of any hydrophobic compounds found in an espresso, whereas filtering the compositions disclosed herein fails to remove the structures produced.

Figure 5:
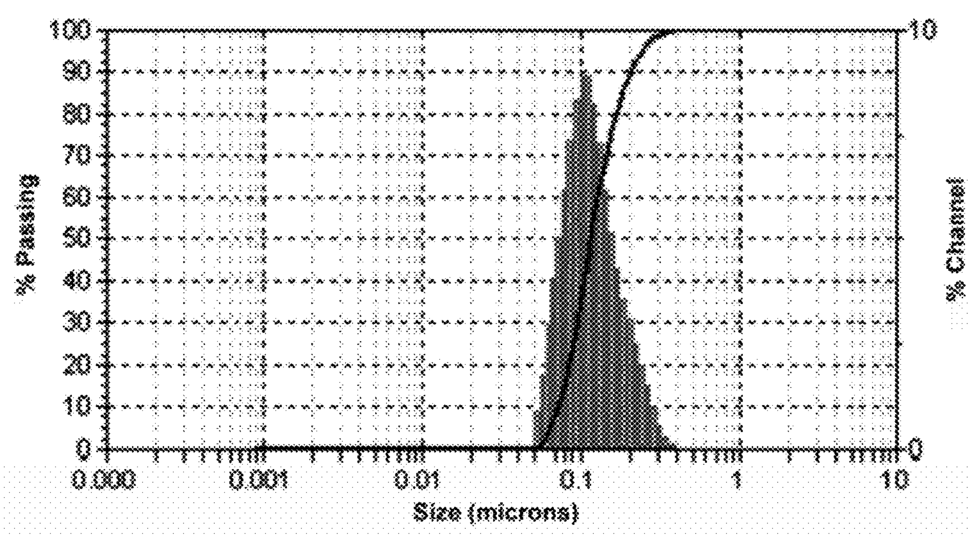
FIG. 5 is a graph showing the particle size of treated (colloidal suspension-added) coffee drink after filtering a 0.22 μm filter.
Figure 6:
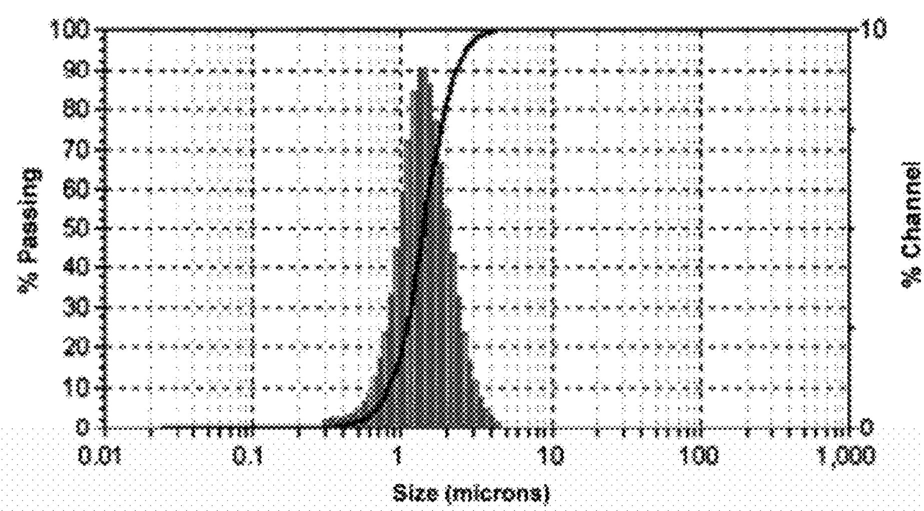
FIG. 6 is a graph showing the particle size of treated (colloidal suspension-added) coffee drink after filtering with a 20 μm filter.

FIGS. 5 and 6 show the results of particle measurements when the colloidal suspension is filtered with a 20 μm filter and a 0.2 μm filter. The measurements were preformed at MicroTrac (Clearwater, Fla.). The average size of the 20 μm filtered sample was 1.2 μm while the 0.2 μm filtered sample produced an average size of 0.12 μm. The addition of hexane to the colloidal suspension doesn't extract any of the hydrophobic (lipid) compounds, showing that the compositions are not a simple emulsion, but a inclusion of the hydrophobic and hydrophilic elements within unique structures; MCMs, MHDs & MECs. Additionally, non-polar and polar aprotic solvents don't break the suspension/emulsion. This colloidal suspension/emulsion doesn't separate or settle with time.

Another key aspect of these compositions and resulting precipitates is that they are stable in both acidic and basic environments as well as increased and decreased temperatures. This allows the composition(s) to remain stable within the digestive tract. The suspension was stable in all acid environments including 50% hydrochloric acid. With bases the suspension was stable up until saponification occurred at 9.2 pH. The only method found to break the suspensions was by adding over 50% of the suspensions volume with 90% ethanol or other alcohol. When the composition(s) suspension is broken, the resulting flocculent/precipitate floats. Adding alcohol to filtered or unfiltered coffee will result in precipitating soluble fiber (polysaccharides), which sinks Because the composition-based precipitates float, it can be concluded that some of the polysaccharides have hydrophobic compounds, like coffee oils, bound in them. When a precipitate created from the composition is separated and washed with hexane, hydrophobic compounds, such as coffee oils, are present. This confirms that some of the polysaccharides have hydrophobic compounds embedded in them. Washing the solute with hexane produces very little free phase coffee oil upon the evaporation of hexane.

Importantly, the overall stability of the compositions is critical to preventing increases in cholesterol and damage to the liver. As stated above, the use of C&K I the human model was ceased after learning that the compounds can cause severe liver toxicity. Once in the digestive tract the compounds remain emulsified. This type of acid-stable emulsion is digested consistently, evenly and at the same time increases gallbladder contractions (Luca Marciani 2007). However, free C&K oils that are present in unfiltered coffee and coffee oil will separate from the hydrophilic phase in the digestive process and float to the upper-layer of the stomach where they are digested last. This delayed digestion adds additional stress to the liver via the continued circulation of bile acids via the ligand ability of Cafestol for FXRs in the distal portion of the small intestines.

Conventional coffee oils, i.e. non-cavitated, do not dissolve in water, therefore, the water-soluble lipid-cleaving enzyme lipase must break it down into digestible compounds. However, lipase requires a water-soluble interface, thus the coffee oil must first be transformed into bile acid micelles. This process doesn't occur until the coffee oil moves into the small intestine where it is exposed to bile acids. As noted above, coffee oil enters the small intestines last because it is hydrophobic and floats in the stomach, so it is digested last. Bile acids are produced by the liver and re-circulated in a process called enteroheptic re-circulation. In order for coffee oil to be transformed into a bile acid micelle, the concentration of bile acid in the small intestine must reach a critical concentration point. Reaching this critical concentration level takes time, and adds to the overall digestion process. This type of digestive activity produces an additional lipid surge on the liver, increases the re-circulation of toxic bile acids, and allows C&K to reach the distal portion of the small intestine prior to complete digestion, where Cafestol has been shown to be an agonist ligand for FXRs.

The disclosed compositions contain MCM structures that present a water-soluble surface area, which allows lipase to begin metabolizing the compounds earlier in digestion. Lipase enzymes are found in the stomach in low concentrations can begin the breakdown the C&K lipid structure within the MCMs. While the MHDs begin to break down via lipase activity in the stomach, this activity is low because lipase needs a water-soluble interface to cleave fatty acids. This reduces the demand for bile acid micelle transformation in the small intestine.

However, because acid-stable emulsions increase gall bladder contractions, which increases the concentration of bile acids in the small intestines, the MHDs are more easily transformed into bile acid micelles. Once the remaining MCMs move into the small intestines they are further broken down by more lipase, which is present in high concentrations in the small intestine. Therefore, the MCMs are rapidly digested and absorbed in the upper half of the small intestine. This dual phase digestion of the MCMs allows C&K to be rapidly and constantly absorbed prior to entering the distal portions of the small intestines.

The MECs and any of the polysaccharide-coated structures produced by the disclosed methods bypass digestion in the stomach and the small intestine. The compositions do not cause an additional lipid load on the liver and do not allow C&K to be absorbed by the distal portion of the small intestine. These structures bring C&K to the colon where bacterial action on the fiber compounds free C&K to be used by the colon cells directly or allow C&K to travel through the portal vein back to the liver. Moreover, the polysaccharides can trap bile and transport it to the colon as well. Additionally, since some of the compositions have both proteins and polysaccharides coated on the outside of said structures, free cholesterol and bile can be trapped in the polysaccharide/protein coatings and transported to the large intestines. By reducing the bile through binding there will be less bile in re-circulation.

Thus, the generated compositions either are quickly and easily digested before entering the small intestine, or bypass digestion in the small intestines, and are instead absorbed in the colon. The compositions therefore prevent the problems associated with the digestion of free phase C&K lipids, which are present in all but filtered coffee (0.2 mg C&K is assumed to be zero). They allow C&K to be safely delivered to the liver and other parts of the body where they can be used therapeutically to increase GSC via up-regulation of the Nrf2 pathway and regulate thiol redox. By regulating thiol redox, these compositions regulate oxidative stress, which is responsible for chronic inflammation. The compositions regulate and reduce the pathology of degenerative and age related disease produced from chronic inflammation by addressing the underpinning cause of the disease; disruption of thiol circuits. Accordingly, the compositions prevent the disruption of thiol circuits thereby reducing, if not preventing, all degenerative and age related diseases.

Additionally, since the disclosed compounds increase GSH, they can also be used to increase GSH production when any activity or stress reduces GSH concentration. It is known that GSH is depleted in endurance athletes. The disclosed compounds can be added to sports drinks or sports gels, which will reduce or prevent the depletion of GSH from the athlete's cells and blood stream.

Though GCS is the rate limiting enzyme in the production/synthesis of GSH, there are other basic compounds that contribute to the production of GSH, such as cysteine, glycine and glutamate. These basic (amino acids) are usually found in diet, however, under stress and poor diet it may be necessary to increase the quantities of these compounds through supplementation. Therefore, all of the composition(s) discussed above can include the addition of either one or a mixture of known GSH building block compounds or compounds that break down to the required compounds, including cysteine, glycine, glutamate, glutamine, N-acetylcysteine, methionine, and synthetic GSH, which breaks down into cysteine, glutamate and glycine in the digestive tract upon ingestion. Additionally, natural polysulfides such as diallyltrisulfide, diallyltetrasulfide can be added to the composition(s) as well. To this extent almost any compound hydrophobic or hydrophilic that can act synergistically with the composition can be add to the composition.

Moreover, because the colloidal particles are acid- and base-stable, any flavor can be added to the suspension produced in examples presented below. Alternatively, to give the suspension other flavors, flavored coffee or instant coffee may be added to it. This would also apply for teas and other extractable compounds used to make any drink. Further, the colloidal suspensions described can be used as a function liquid food additive for semisolid food products, such as yogurt, cheeses, creams, orange juice, sports drinks or sports gels.

It is noted that a scaled down version of the following procedures may be used for non-commercial preparation, albeit with lower yields. To exponential increase removal of hydrophobic and hydrophilic compounds cavitation technologies, mostly in the form of low frequency ultrasound, the inclusion of a cavitation system can be incorporated into all of today's standard methods of brewing coffee, causing the coffee to possess the previously described complexes. This allows the healthy hydrophobic and hydrophilic compounds of the coffee bean or compounds added to the bean or solution to be transformed into MCMs, MECs and MHDs. While this increase doesn't necessarily increase the taste of the coffee it does increase the health benefits.

Because of the vast number of different coffee brewing process ultrasonic horns and/or disc can be placed in many different orientations. The horns and discs can also vary in size, shape and thickness. Moreover, the pulse time/type and frequencies can also vary. The pulse time can be 0 seconds to 1 hour and can be stepped up or down through the entire processing event. The type of frequency can be square or amplitude. The frequency can by 15 k hertz to 2.5 M hertz. Multiple frequencies and powers can be use simultaneously or intermediately mixed. The over all process time can vary from seconds to days. Additionally other cavitation techniques can be used as well such as a homogenizer liquid whistle or an air spray atomizer. Again these devices can be placed in many different positions and locations and be engineered to fit the specific brewing process. Anyone skilled in the art of cavitational science can easily engineer the integration of said technologies into all brewing machines and process.

Example 1

Figure 7:
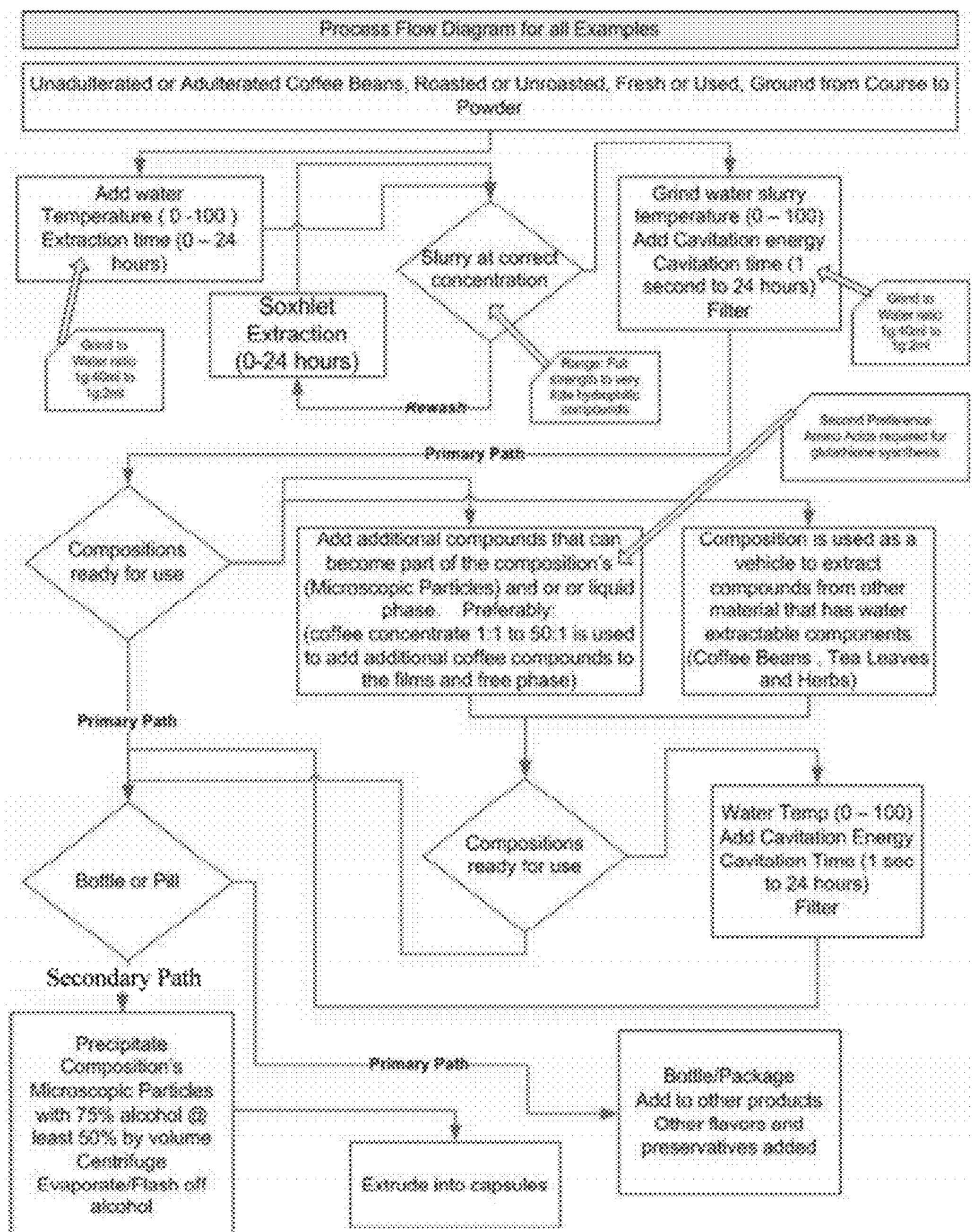
FIG. 7 is a process flow diagram of the invention.

As seen in FIG. 7, powdered to coarse-ground roasted or unroasted coffee beans which were un-adulterated or adulterated with other soluble or insoluble compounds were added to water between about 0° C. to about 100° C. The ratio of grind to water ranged from 1 g:40 ml to 1 g:2 ml with the effective ration at 1 g:20 ml. In this example the beans were unadulterated roasted course ground and the ratio used was 1 g:40 ml. However, it is noted that the temperature of the water controls extraction rates, not extraction amounts. Higher extraction rates occur at higher water temperatures. Accordingly, any temperature water may be used in the extraction process, including chilled water. The coffee grounds remained in the water extraction for about 1 minute to 72 hours, with an effective extraction time of 6 minutes. Other food grade and heath components are optionally added after the water extraction, thereby permitting incorporation of these components into the micelles films, lipid droplets films, and soluble fiber matrix. Upon completion of the first extraction, the hydrated bean grounds are exposed to ultrasonic cavatation energy, from between 15 Khz-100 Mhz, with the optimal frequency of 40 Mhz at 200 watts (power and horn shape can vary according to scale). The temperature can range from about 0° C. to about 100° C. The bean grounds were exposed to the cavitation processing for from about 1 second to about 72 hours, with the effective range at 5 minutes. The resulting suspension was then permitted to settle, followed by filtering to remove fines down to 40 micrometers.

Example 2

Powdered to coarse-ground used or previously water extracted, i.e. brewed, roasted or unroasted coffee beans, were added to water with a temperature between about 0° C. to about 100° C. The ratio of grind to water ranged from 1 g:40 ml to 1 g:2 ml with the effective ration at 1 g:20 ml. This process of water extraction was used 6 to 10 times or until the majority of water soluble compounds were removed from the beans. Soxhlet extraction (Soxhlet, 1879, 232, 461) may be used to enhance removal and reduce the amount of water required. The eluent produced, containing water soluble coffee compounds, may be discarded or separated to be reused as components for the food and beverage industry.

The washing of the coffee bean grounds exposes bean fibers to water for over 8 hours to about 24 hours, allowing insoluble and soluble fibers of the bean to swell to their maximum. The fully hydrated beans were then exposed to ultrasonic energy, from between 15 kHz-100 mHz, with the optimal frequency of 40 kHz at 200 watts. Exposure times were the same as in example 1. The bean to water ratio was 1 g:20 ml though it can range from 1 g:40 ml to 1 g:2 ml. The water temperature was the same as example 1. Cavitation energy also extracted additional insoluble and soluble fiber from the hydrated beans. Ultimately, the micelles or lipid droplets or soluble fiber matrix in the suspension contain monomolecular or mutimolecular films, which contain proteins, esterfied and free form Cafestol and Kahweol, amino acids, fatty acids, waxes, and soluble fiber and insoluble fiber found in coffee. While compounds like coffee acids and caffeine are almost completely removed. After settling, the suspension was filtered to remove fines up to 40 micrometers.

Example 3

The resulting colloidal suspension from example 1 or 2 was added to standard water extracted coffee, i.e. brewing, or coffee compounds from roasted or unroasted beans (standard filtered or unfiltered). The colloidal suspension/coffee drink mixture was then exposed to cavitation by ultrasound so that both non-soluble and soluble compounds are added to the film, thereby increasing film size, distribution and compound type. The higher the concentration profile the greater the films. The standard water extraction was concentrated from 1:1 up to 50:1. The greater the concentration the greater the films produced on the microscopic particles. To enhance film development and embedments, cavitation is optionally repeated as an additional step.

To attach different compounds to the film or soluble fiber matrix, other extractable natural compounds can be added to the colloidal suspension prior to cavatation. Examples of such extractable materials include teas and herbs. Advantageously, their use can increase the colloidal (i.e. Micelle and Lipid proplet) films. Further, the addition of optional natural and/or synthetic compounds to the colloidal suspension results in increased film-type and soluble fiber embedment of added compounds. To enhance film development and embedments cavation is repeated as an additional step.

Example 4

Flavors can be added to the acid and base stable colloidal suspensions produced in example 1, 2 and 3. Alternatively to give the suspension flavor the suspension itself can be used to as an extraction liquid to brew coffee or instant coffee can be added to it. The temperature can range from 0° C. to about 100° C. The suspensions can also be added to any other water extractable compounds to extract the extractable compounds like tea to make any health drink based on the suspension's microscopic particles. The suspension has unique extracting qualities because of its unique structures. Additionally because the suspension is lipid and soluble fiber based they give an enhanced mouth feel to any drink produced.

Example 5

The colloidal suspensions and their unique microscopic particles produced in examples 1, 2, 3 and 4 can be used as a functional liquid food additive such as in yogurt, or orange juice.

Example 6

Oral medicaments, such as pills, may be prepared comprising the extracts described above. Once the colloidal suspension was generated, 75% alcohol was added at a ratio of at least 50:50 to break the suspension. The resulting precipitate was centrifuged and dried to remove the majority of the alcohol to form a flowable concentrate which was added into capsules. Alternatively, the precipitate was completely dried and transferred into solid pill form. It is noted the suspensions may be dried with any standard drying techniques including freeze drying, instead of the centrifugation or evaporation.

Uniquely these compositions can be used to deliver 50 mg, 100 mg or 200 mg of C&K per administration. Compared to a filtered cup of coffee it would take 250, 500 and 1000 cups of filtered coffee to reach these C&K levels. Most importantly, the C&K from filtered coffee or unfiltered coffee is in a free phase oil form, which would result in the aforementioned liver toxicity. Processing with cavitation technologies produced new unique structures and compositions containing C&K, which enable safe and effective regulation of thiol redox.

To verify that the disclosed compositions regulated thiol redox, without negatively impacting the liver or cholesterol/LDL production, specific biomarkers were chosen to monitor individual healthy volunteers who consumed the compositions. A standard cholesterol panel was performed to monitor cholesterol, LDL, HDL and triglycerides. A standard liver panel was performed to monitor alanine aminotransferase (ALT), aspartate aminotransferase (AST), alkaline phosphatase (ALP) and bilirubin. For thiol redox regulation both γGlutamyl transferase/γGlutamyl transpeptidase (GGT) and Lipoprotein (a) (Lp(a)) were used.

The functions of GGT have been discussed previously, however, it needs to be pointed out that GGT contains a thiol group and therefore GGT itself is regulated by thiol redox. Currently, there are no FDA approved drugs or supplements that significantly reduce GGT levels.

Lp(a) contains a disulfide thiol bridge that connects the Apolipoprotein B subunit to Apoprotein (a), which is regulated by thiol redox. Elevated levels of LPa increase the risk of death from CVDs by 166% regardless/independent of cholesterol and LDL levels. (Ariyo 2003) Importantly, currently there are no drugs or supplements that significantly reduce Lp(a) levels. Naicin, with its flushing and intestinal side effects has been shown at high levels to slightly reduce Lp(a) levels by up to 15%.

Testing was performed with the different composition(s) to monitor cholesterol and liver damage. Volunteers were both male and female and had a history of drinking at least one cup of filtered coffee per day for over 5 years. The ages ranged from 44 to 71. Volunteers were asked to consume coffee containing the disclosed compositions. At all levels of consumption (200 ml/day to 1 liter/day) there was no significant increase or decrease in cholesterol or LDL levels, while main liver enzyme biomarkers were reduced, as seen in Table 3. At the same consumption levels GGT was reduced up to 300% while Lp(a) was reduced up to 60%.

TABLE 3

A correlation of liver biomarkers affected by administration of the disclosed compositions containing Cafestol and Kahweol.

| Liver Biomarker | Decrease from endogenous level |
|---|---|
| Alanine Aminotransferase (ALT) | 50%, |
| Aspartate Aminotransferase (AST) | 64%, |
| Alkaline Phosphatase (ALP) | 72% |
| Bilirubin | 67%. |

After analysis of the positive results on healthy volunteers, it was determined to test the compositions on an unhealthy volunteer. This volunteer suffered from severe liver cirrhosis brought on by Hepatitis C, and acute food poisoning that produced sepsis/blood poisoning which severally damaged the liver. Prior to consumption, this volunteer's AST and ALT levels were elevated up to 6 times the upper limit, and has begun applying for a liver transplant. The cut off for AST is 40 units per liter (UL) while the cut off for ALT is 55 UL. The volunteer consumed 200 ml per day of the disclosed compounds, and enzyme levels recorded, as seen in Table 4.

TABLE 4

A correlation of liver protein levels affected by administration of the disclosed compositions containing Cafestol and Kahweol.

| | Date | | |
|---|---|---|---|
| Enzyme | Feb. 27, 2009 | Mar. 12, 2009 | Apr. 9, 2009 |
| Protein, Serum | 7.3 | 7.1 | 6.9 |
| Albumin | 2.6 | 2.8 | 2.7 |
| Bilirubin | 2.3 | 2.3 | 1.2 |
| Bilirubin Direct | 0.8 | 0.8 | 0.5 |
| APS | 72 | 72 | 85 |
| AST | 234 | 192 | 156 |
| ALT | 149 | 131 | 102 |
| GGT | 51 | 54 | 55 |

Bilirubin was decreased by 92% while AST and ALT were reduced by 50% and 46% respectively. While there is no cure for Cirrhosis of the Liver except for a liver transplant, the protein levels are trending in the correct direction. However, reversal of cirrhosis will not be available until all markers are reduced and an additional liver biopsy is performed.

The biomarker homocysteine contains a thiol, and therefore should be reduced as well. The biomarker C-reactive protein is directly related to the liver and should be reduced as well. Moreover, epidemiology studies indicate that both of these biomarkers have been reduced by simple coffee consumption. These biomarkers and additional biomarkers will be tested in upcoming studies with the disclosed compositions. In fact, because the compositions regulate thiol redox, all biomarkers that are directly or indirectly related to Thiol Redox will be regulated by the disclosed compositions.

REFERENCES

1. Luca Marciani: Enhancement of intragastric acid stability of a fat emulsion meal delay gastric emptying and increases cholecystonkinin release and gallbladder contraction, 2007
2. Soxhlet, Die gewichtsanalytische Bestimmung des Milchfettes, Polytechnisches J. (Dingler's) 1879, 232, 461

Glutathione and REDOX

1. Dean P. Jones: Radical-free biology of oxidative stress, 2008
2. Francesco Cimino: Glutathione metabolism: Favorable versus unfavorable effects, 2008
3. Albert van der Vliet: Cellular and environmental electrophiles: Balancing redox signaling, inflammation, and cell death pathways, 2008
4. Danyelle M. Townsend: S-Glutathionylation Indicator if cell stress and regulator of the unfolded protein response, 2007
5. Callum Livingstone: Targeting therapeutics against glutathione depletion in diabetes and its complications; 2007
6. Rosenblat Mira: Anti-oxidant and anti-atherogenic properties of liposomal glutathione: Studies in vitro, and in the atherosclerotic apolinprotein E-deficient mice, 2007
7. Jessica Gutierrez: Free radicals, mitochondria, and oxidized lipids: The emerging role in signal transduction in vascular cells, 2006
8. Ranieri Rossi: Oxidized forms of glutathione in peripheral blood and biomarkers for oxidative stress. 2006
9. Salman Ashfaq: The relationship between plasma levels of oxidized and reduced thiols and early Atherosclerosis in healthy adults, 2006

10. Rangasamy Sampathkumar: Increased glutathionylated hemoglobin (HbSSG) in type 2 diabetes subjects with microangiopathy, 2005
11. Niture S. K.: S-thiolathion mimicry: quantitative and kinetic analysis of redox status or protein cysteines by glutathione-affinity chromatography, 2005
12. Zilmer, M: The glutathione system as an attractive therapeutic target, 2005
13. Nalini Santanam: Cellular cysteine generation does not contribute to the initiation of LDL oxidation, 1995

Epidemiology of Coffee

1. Erika Bageman: Coffee consumption and CYP1A2*1F genotype modify age at breast caner diagnosis and estrogen receptor status, 2008
2. Science Daily: Coffee drinkers have slightly lower death rates, study finds, 2008
3. Gang Hu: Joint effects of coffee consumption on serum gamma-glutamyltransferase on the risk of liver cancer, 2008
4. Science Daily: Higher coffee consumption associated with lower liver cancer risk, 2008
5. Carlo La Vecchia: Cancer and liver cancer prevention: Is it a fact or just potential?, 2008
6. Perth Happonen: Coffee consumption and mortality in a 14 year follow up of elderly northern Finnish population, 2008
7. Kotani K.: The relationship between usual coffee consumption and serum C-reactive protein level in Japanese female population, 2008
8. S. H. Cadden: Possible beneficial effect of coffee on liver disease and function, 2007
9. Judith Groch, MedPage Today: Analysis validates reduced risk of liver cancer by coffee drinking, 2007
10. ABC Online. Coffee 'lowers liver cancer risk', 2007
11. Colorectal Cancer Association of Canada: Coffee drinking no longer so controversial, 2007
12. Science Daily: Drinking four or more cups of coffee a day may prevent gout, 2007
13. Susanna C. Larsson: Coffee consumption and risk of liver cancer: A meta-analysis, 2007
14. Kraft Foods: Health benefits of coffee: A review of existing and emerging science, 2007
15. Francesca Bravi: Coffee drinking and hepatocellular carcinoma risk: A meta-analysis, 2007
16. Maria Giuseppina Silletta: Coffee consumption and risk of cardiovascular events after acur myocardial infraction: Results from the GISSI Prevenzione trail, 2007
17. N. C. McAvoy: Coffee is good for the liver, 2006
18. Sarah A. Rosner: Coffee consumption and risk of myocardial infraction among older Swedish women, 2006
19. Trine Ranheim: Coffee consumption and human health—beneficial or detrimental?—Mechanisms for effects of coffee consumption on different risk factors for cardiovascular disease and type 2 diabetes mellitus, 2005
20. Rob M van Dam: Coffee consumption and risk of type 2 diabetes: A systematic review, 2005
21. Editorial (journal of hepatology): Coffee, liver enzymes, cirrhosis and liver cancer, 2005
22. Jaakko Tuomilehto: Coffee consumption and risk of type 2 diabetes mellitus among middle-aged Finnish men and women, 2004
23. Silvano Gallus: Does coffee protect against liver cirrhosis?, 2002
24. Marina J. Grubben: Unfiltered coffee increases plasma homocysteine concentrations in healthy volunteers: A randomized trail, 2000
25. Edward Giovannucci: Meta-analysis of coffee consumption and risk of colorectal cancer, 1998
26. John A. Baron: Coffee, tea, tobacco and caner of the large bowel, 1994
27. Javier Pintos: Mate' coffee, and tea consumption and risk of cancers of the upper aerodigestive tract in southern Brazil, 1994
28. E. Casiglia: Unexpected effect of coffee consumption on liver enzymes, 1993

C&K studies

1. Salminen: Terpeniods: Natural inhibitors of NF-kB signaling with ant-inflammatory and anticancer potential, 2008
2. Yong Pil Hwang: The coffee diterpene Kahweol induces heme oxygenase-1 via the PI3K and p38/Nrf2 pathway to protect human dopaminergic neurons form 6-hydroxydopamine-drived oxidative stress, 2008
3. Larry G. Higgins: Induction of cancer chemopreventive enzymes by coffee in mediated by transcription factor Nrf2. Evidence that the coffee specific diterpenes C&K confer protection against acrolein, 2008
4. Wolfgang W. Huber: Effects of coffee and its chemoprotective components Kahweol and Cafestol on cytochrome P450 and sulfotransferase in rat liver, 2008
5. Marie-Louise Ricketts: The cholesterol raising factor from coffee beans, as an agonist ligand for the farnesoid and pregane x receptors, 2007
6. J. Bichler: Coffee consumption protects human lymphocytes against oxidative and 3-amino-1-methyl-5H-pyrido [4,3-b]indole acetate (Trp-P-2) induced DNA damage: Results of an experimental study with human volunteers, 2007
7. Christophe Cavin: Reduction in antioxidant defenses many contribute to ochratoxin a toxicity and carcinogenicity, 2007
8. Kyung Jin Lee: Hepatoprotective an antioxidant effects of the coffee diterpenes Kahweol and Cafestol on carbon tetrachloride-induced liver damage in mice, 2007
9. Wolfgang W Huber: Pretreatment of rats with coffee components Kahweol and Cafestol protects against liver damage and oxidative stress that occur within 48 hours after exposure to carcinogenic azoxymethone, 2006
10. Wolfgang W. Huber: Modification of N-acetyltransferase and glutathione S-transferases by coffee components: possible relevance for cancer risk, 2006
11. Ji Young Kim. Inhibitory effect of coffee diterpene Kahweol on carrageenan-induced inflammation in rats, 2006
12. Sun Young Choi: Protective effect of the coffee diterpenes Kahweol and Cafestol on tert-butyl hydroperoxide-induced oxidative hepatotoxicity, 2006
13. Hyung Gyun Kim: The coffee diterpene Kahweol inhibits tumor necrosis factor-a-induced expression of cell adhesion molecules in human endothelial cells, 2006
14. B. J. Majer: Coffee diterpenes prevent the genotoxic effects of 2-amino-1-methyl-phenylimidazo[4,5-b]pyridine (PhIP) and N-nitrosodimethylamine in human derived liver cell line (HepG2), 2005
15. Hans Steinkellner: Coffee consumption induces GSTP in plasma and protects lymphocytes against anti-benzo[a] pyrene-7,8-dihydrodiol-9,10-epoxide induced DNA damage: Results of controlled human interventions, 2005
16. Beatrice Pool-Zobel: Modulation of xenbiotic metabolizing enzymes by anticarcinogens-focus on glutathione S-transferase and their role a targets of dietary chemoprevention in colorectal carcinogenesis, 2005
17. Mark V. Beokschoten: Coffee oil consumption increases plasma levels of 7a-hydroxy-4-cholestin-3-one in humans, 2005

18. Mark V. Beokschoten: Coffee bean extracts rich and poor in Kahweol give rise to elevation of liver enzymes in healthy volunteers, 2004

19. Ji Young Kim: The coffee diterpene Kahweol suppress the inducible nitric oxide synthase expression in macrophages, 2004

20. Ji Young Kim: Suppressive effects of the Kahweol and Cafestol on cyclooxygenase-2 expression in macrophages, 2004

21. Wolfgang W. Huber: Potential chemoprotective effects of the coffee components Kahweol and Cafestol palmitates via the modification of hepatic N-acetyltransferase and glutathione S-transferase activities, 2004

22. Philip Lannaccone (National Institute of Environmental Health Sciences):

Environmental medicine: Where are we and where do we go from here? (You can't navigate from lost), 2004

23. Robert J. Turesky: The effects of coffee on enzymes involved in metabolism of the dietary carcinogen 2-amino-1-methyl-6-phenylimidazo [4,5-b]pyridine in rats, 2003

24. F. Esposito: Moderate coffee consumption increases plasma glutathione but not homocysteine in healthy subjects, 2003

25. Veronika Somoza: Activity-guide identification of a chemoprotective compound in coffee beverage using in vitro and in vivo techniques, 2003

26. Gerlinde Scharf: Enhancement of glutathione an gamma-glutamylcysteine synthetase, the rate limiting enzyme of glutathione synthesis, by chemoprotective plant-derived food and beverage components in the human hepatoma cell line HepG2, 2003

27. C. Cavin: Coffee diterpenes prevent benzo[α]pyrene genotoxicity in rat and human culture systems, 2003

28. Wolfgang W. Huber: Coffee and its chemoprotective components Kahweol and Cafestol increase the activity of 06-methylguanine-DNA methyltransferase in rat liver—comparison with phase II xenobiotic metabolism, 2003E. Strandhagen: Filtered coffee raises serum cholesterol: results from a controlled study, 2003

29. Mark V. Beokschoten: Reproducibility of the serum lipid response to coffee oil in healthy volunteers, 2003

30. Hammar N.: Association of boiled and filtered coffee with incidence of first nonfatal myocardial infraction: the SHEEP and VHEEP study, 2003

31. Wolfgang W. Huber. Enhancement of the chemoprotective enzymes glucuronosly transferase and glutathione transferase in specific organs of the rat by the coffee components Kahweol and Cafestol, 2002

32. Wolfgang W. Huber: The coffee components Kahweol and Cafestol induce gamma-glutamylcysteine synthetase, the rate limiting enzyme of chemoprotective glutathione synthesis, in several organs of the rat, 2002

33. C. Cavin: Cafestol and Kahweol, two coffee specific diterpenes with antic arcinogenic activity, 2002

34. Michael McMahon: The cap 'n' collar basic leucine zipper transcription factor Nrf2 controls both constitutive and inducible expression of intestinal detoxification and glutathione Biosynthetic enzymes, 2001

35. M. J. A. L. Grubben: The effect of unfiltered coffee on potential biomarkers for colonic cancer risk in healthy volunteers: a randomized trial, 2000

36. Albert A. van Zeeland: 8-Hydroxydeoxyguanosine in DNA from leukocytes of healthy adults: relationship with cigarette smoking, environmental tobacco smoke, alcohol and coffee consumption, 1999

37. C. Cavin: The coffee-specific diterpenes C&K protect against aflatoxin B1-induced genotoxicity through a dual mechanism, 1998

38. B. De Roos: Absorption and urinary excretion of the coffee diterpenes C&K in healthy ileostomy volunteers, 1998

39. Benoit Schilter: Placental glutathione S-transferase (GST-P) induction as a potential mechanism for the anti-carcinogenic effect of the coffee specific components Cafestol and Kahweol, 1996

40. B. De Roos: Consumption of French-pressed coffee raises cholesteryl ester transfer protein activity levels before LDL cholesterol in normolipidaemic subjects, 2000

41. R. Urgert: Diterpenes from coffee beans decrease serum levels of lipoprotein(a) in humans: results from four randomized controlled trials, 1997

42. R. Urgert: Comparison of effect of cafetiere an filter coffee on serum concentration of liver aminotransferases and lipids: six month randomized controlled trial, 1996

43. R. Urgert: The cholesterol-raising factor from coffee beans, 1996

44. Kaare Bonaa: Coffee and cholesterol: Is it all in the brewing? The Tromso study, 1988

45. Trine Ranheim: Effect of a coffee lipid (Cafestol) on regulation of lipid metabolism in Ca—Co-2 cells, 1995

46. Van Rooij, Univ. hosp. Leiden, cent. human drug res., dep. cardiology, Leiden, PAYS-BAS; A placebo-controlled parallel study of the effect of two types of coffee oil on serum lipids and transaminases: identification of chemical substances involved in the cholesterol-raising effect of coffee, The American journal of clinical nutrition, 1995; 61:1277-83

47. Mensink R P, Department of Human Nutrition, Agricultural University, Wageningen, The Netherlands, Diterpene composition of oils from Arabica and Robusta coffee beans and their effects on serum lipids in man, Journal of Internal Medicine, 1995: 237:6:543-50

GGT

Okan Turgut: Letter to the editor Atherosclerosis—Gamma-Glutamyltransferase as a useful predictor of cardiovascular risk: Clinical and epidemiology perspectives, 2008

1. Alexander M. Strasak: Longitudinal change in serum Gamma-Glutamyltransferase and cardiovascular disease mortality: a prospective population-based study in 76,113 Austrian adults, 2008

2. Lee Yong-Jae: Association of serum Gamma-Glutamyltransferase with C-reactive protein in Korean adults, 2008

3. G. Zoppini: Relationship between soluble CD40 ligand and Gamma-Glutamyltransferase concentrations in non-drinking, young type 1 diabetic individuals, 2008

4. Alexander M. Strasak: Prospective study of the association of Gamma-Glutamyltransferase with cancer incidence in women, 2008

5. Abstract: Including abnormal liver function tests in the definition of metabolic syndrome its predictive nature for cardiovascular disease, 2008

6. Alexander M. Strasak: Association of Gamma-Glutamyltransferase and risk of cancer incidence in men: a prospective study, 2008

7. S. G. Wannamethee: The value of Gamma-Glutamyltransferase in cardiovascular risk prediction in men without diagnosed cardiovascular disease or diabetes, 2008

8. Maria Franzini: Gamma-Glutamyltransferase activity in human atherosclerotic plaques—biochemical similarities with the circulating enzyme, 2008

9. Philippe Giral: Elevated Gamma-Glutamyltransferase activity and perturbed thoil profile are associated with features of metabolic syndrome, 2008

10. Duk-Hee Lee: Letter to the editor Arterioscler Thromb Vasc Biol. —Is Gamma-Glutamyltransferase a biomarker of xenobiotics, which are conjugated with glutathion?, 2008

11. Burcu Balam Yavuz: Serum elevated Gamma-Glutamyltransferase levels may be a marker for oxidative stress in Alzheimer's disease, 2008

12. Douglas Lee and R Vasan: Gamma-Glutamyltransferase and metabolic syndrome, cardiovascular disease, and mortality risk: the Framingham heart study, 2007

13. Giuseppe Lippi: Relationship between Gamma-Glutamyltransferase, lipids and lipoprotein(a) in the general population, 2007

14. Kiyoshi Hiramatsu: Overexpression or Gamma-Glutamyltransferase in transgenic mice accelerates bone resorption and causes osteoprosis, 2007

15. Alfonso Pompella: Gamma-Glutamyltransferase, redox regulation and cancer drug resistance, 2007

16. Kazuhiko Kotani: Letter to the editor clinica chimica acta—Changes in serum Gamma-Glutamyltransferase levels in subjects with normal blood pressure and prehypertension, 2007

17. M C. Devers: Should liver function tests be included in definitions of metabolic syndrome? Evidence from the association between liver function tests, components of metabolic syndrome and prevalent cardiovascular disease, 2007

18. Anoop Shankar: Association between serum Gamma-Glutamyltransferase level and prehypertension among US adults, 2007

19. Scott M. Grundy: Gamma-Glutamyltransferase another biomarker for metabolic syndrome and cardiovascular risk, 2007

20. Lili Kazemi-Shirazi: Gamma-Glutamyltransferase and long-term survival: Is it just the liver?, 2007

21. Yutaro Asaba: Urinary Gamma-Glutamyltransferase as a potential marker of bone resorption, 2006

22. Michele Emdin: Gamma-Glutamyltransferase as a cardiovascular risk factor, 2006

23. Seungho Ryu: Gamma-Glutamyltransferase as a predictor of chronic kidney disease in nonhypertensive and nondiabetic Korean men, 2006

24. Aldo Paolicchi: B-lipoprotein and LDL associated serum Gamma-Glutamyltransferase in patients with coronary Atherosclerosis, 2006

25. Elfriede Ruttmann: Gamma-Glutamyltransferase as a risk factor for cardiovascular disease mortality—an epidemiology investigation of a cohort of 163,944 Austrian adults, 2005

26. Michele Emdin: Editorial Circulation—Gamma-Glutamyltransferase, Atherosclerosis, and cardiovascular disease, 2005

27. Aldo Paolicchi: Human atherosclorotic plaques contain Gamma-Glutamyltransferase enzyme activity, 2004

28. Alfonso Pompella: The significance of serum Gamma-Glutamyltransferase in cardiovascular diseases, 2004

29. Mojgan Djavaheri-Mergny: Gamma-Glutamyltransferase activity mediates NF-kB activation through lipid peroxidation in human leukemia U937 cells, 2002

30. John B. Whitfield: Genetic covariation between serum Gamma-Glutamyltransferase and cardiovascular risk, 2002

31. Michele Emdin: Prognostic value of serum Gamma-Glutamyltransferase activity after myocardial infraction, 2002

32. Mason J E, Berkeley HeartLab, Inc.; γ-glutamyltransferase: a novel cardiovascular risk biomarker, Preventive Cardiology 2010: 13:1:36-41.

33. Tatjana Stojakovic, Clincal Institute of Medical Chemistry, Medical University of Graz, Graz, Austria; Serum γ-glutamyltransferase and mortality in persons undergoing coronary angiography—The Ludwigshafen Risk and Cardiovascular Health Study, Atherosclerosis 2010: 208:2:564-571.

34. L. P Breitling, Division of Clinical Epidemiology, German Cancer Research, Heidelberg, Germany; γ-glutamyltransferase and prognosis in patients with stable coronary heart disease followed over 8 years, Atherosclerosis 2010: Jan. 11 Online 2010.

35. Yuji Shimizu, Department of Social and Environmental Medicine, Osaka University, Osaka Japan; γ-glutamyltransferase and Incident Stroke Among Japanese Men and Women, Stroke AHA 2010: 41:385-388.

36. Franzini M, Cardiovascular risk factors and γ-glutamyltransferase fractions in healthy individuals, Clinical Chemistry and Laboratory Medicine 2010: Online February 2010.

37. Sen N, Department of Cardiology, Heart-Education and Research Hospital, Ankara, Turkey, Relationship between elevated serum γ-glutamyltransferase activity and slow coronary flow, Turkish Society of Cardiology 2009: 37:168-173.

38. Gerhard Poelzl, Innsbruck Medical University, Austria; Prevalence of elevated γ-glutamyltransferase (GGT) and prognostic significance of GGT in chronic heart failure, Circulation: Heart Failure 2009: 2:294-302.

39. Panagiotis Korantzopoulos, Department of Cardiology, University of Ioannina, Ionnina, Greece; Association Between Serum γ-Glutamyltransferase and Acute Ischemic Nonembolic Stroke in Elderly Subjects, Archives of Medical Research 2009: 40:7:582-589.

40. Okan Turgut, Department of Cardiology Cumhuriyet, Sivas, Turkey; Association of γ-Glutamyltransferase with Cardiovascular Risk: A Prognostic Outlook, Archives of Medical Research 2009: 40:4:381-320.

41. Michelle Emdin, CNR Institute of Clinical Physiology, Pisa, Italy; Additive Prognostic Value of gamma-glutamyltransferase in Coronary Artery Disease, International Journal of Cardiology, 2009: 136:1:80-85.

42. D-H Lee, Journal of Epidemiology and Community Health; Serum γ-glutamyltransferase: new insights about an old enzyme 2009; 63:884-886.

43. Lee, Joeng Gyu, Center for Obesity Pusan Hospital, South Korea; Multiple biomarkers and their relative contributions to identifying metabolic syndrome, International Journal of Clincal Chemistry 2009; 408:1-2:

44. Abigail, Fraser, Medical Research Counsel Center for Casual Analysis in Translational Epidemiology, University of Bristol, Bristal, UK; Alanine Aminotransferase, γ-Glutamyltransferase, and Incident Diabetes, Diabetes Care 2009: 32:4741-750.

45. Constance E. National Institutes of Health, Bethesda; Elevated serum alanine aminotransferase and γ-glutamyltransferase and mortality in the United States, Gasteroenterology 2009: 136:477-485.

46. Turay Yardimci, Department of Biochemistry, Faculty of Pharmacy, Marmara University, Istanbul, Turkey; Characterization of Platelet Gamma Glutamyltransferase and Its Alteration in Cases of Atherosclerosis, Clincal and Applied Thrombosis, 1995:1:2:103-113.

Lipoprotein (a)

1. Williams Davis: What your doctor didn't tell you about lipoprotein (a), 2008
2. Serena Gordan: Little known fat can be a heart breaker—elevated lipoprotein (a) levels boost cardiovascular disease risk for some, 2008
3. Claes Bergmark: A novel function of lipoprotein (a) as a preferential carrier of oxidized phospholipids in human plasma, 2008
4. Peter H Jones: lipoprotein (a) and coronary artery disease: "little" is more, 2008
5. Anna Bennet: lipoprotein (a) levels and risk of future coronary heart disease—large scale prospective data, 2008
6. J. Staples: Progressive kidney disease in three sisters with elevated lipoprotein (a), 2008
7. Nilis H Petersen: Lp(a) lipoprotein and plasminogen activity in patients with different etiology of ischemic stroke, 2007
8. Gregory T Jones: Plasma lipoprotein (a) indicates risk for 4 distinct forms of vascular disease, 2007
9. Katrin Uhlig: Cross-sectional characterization of lipoprotein (a) in chronic kidney disease, 2005
10. Giuseppe Lippi: lipoprotein (a): an emerging cardiovascular risk factor, 2003
11. Abraham A Ariyo: Lp(a) lipoprotein, vascular disease and mortality in the elderly, 2003
12. Jianqiu Pan: Extended-release niacin treatment of the atherogenic lipid profile and lipoprotein (a) in diabetes, 2002
13. Jianqiu Pan: Niacin treatment of the atherogenic lipid profile and Lp(a) in diabetes, 2002
14. ACC News Release: High lipoprotein (a) level increases men's risk of heart problems, 2001
15. Jay Edelberg: Why is lipoprotein (a) relevant to thrombosis?, 1992

In the preceding specification, all documents, acts, or information disclosed do not constitute an admission that the document, act, or information of any combination thereof was publicly available, known to the public, part of the general knowledge in the art, or was known to be relevant to solve any problem at the time of priority.

The disclosures of all publications cited above are expressly incorporated herein by reference, each in its entirety, to the same extent as if each were incorporated by reference individually.

While there has been described and illustrated specific embodiments of methods of manufacturing, and compositions of Cafestol and Kahweol, which are useful for the treatment of degenerative diseases, it will be apparent to those skilled in the art that variations and modifications are possible without deviating from the broad spirit and principle of the present invention. It is also to be understood that the following claims are intended to cover all of the generic and specific features of the invention herein described, and all statements of the scope of the invention which, as a matter of language, might be said to fall therebetween.

What is claimed is:

1. A composition of an extract of coffee beans comprising Cafestol and Kahweol, formed by the steps:

grinding roasted or unroasted coffee beans;

washing the coffee bean grounds in water to yield extracted coffee beans;

exposing the hydrated bean grounds to cavitation at 15 khz to 100 mhz;

wherein the cavitation forms a micelle with a core comprising cafestol and kahweol and an outer coating comprising polysaccharide, melanoidin, or a combination thereof;

allowing the resulting suspension to settle; and filtering the resulting suspension to 40 micrometers.

2. The composition of claim 1, wherein the ground roasted or unroasted coffee beans are between powdered to coarse-ground.

3. The composition of claim 1, wherein the water is between about 0° C. to about 100° C.

4. The composition of claim 1, wherein the water wash is conducted for between about 1 minute to 72 hours.

5. The composition of claim 1, further comprising performing a Soxhlet extraction after the washing step.

6. The composition of claim 1, wherein the cavitation is performed at 40 Mhz at 200 watts.

7. The composition of claim 1, wherein the temperature of the cavitation is between about 0° C. to about 100° C.

8. The composition of claim 1, wherein the coffee bean grounds are exposed to cavitation from about 1 second to about 72 hours.

9. The composition of claim 1, wherein the composition further comprises additional hydrophobic compounds, hydrophilic compounds, melanoidin, proteins polysaccharides, melanoidins, or combinations thereof.

10. The composition of claim 1, further comprising a film comprising proteins, amino acids, polysaccharides, melanoids, or combinations thereof.

11. The composition of claim 1, further comprising cysteine, glycine, glutamate, glutamine, N-acetylcysteine, methionine, synthetic GSH, natural polysulfides, diallyltrisulfide, diallyltetrasulfide, or combinations thereof;

wherein these components are added to the extracted coffee beans before exposing the coffee beans to cavitation.

12. The composition of claim 1, wherein the composition is added to a base food product, wherein the food product is flavored coffee, instant coffee, tea, yogurt, cheese, dairy, orange juice, sports drinks, sports gels, or pills.

* * * * *